United States Patent [19]
Katsuya et al.

[11] Patent Number: 5,233,089
[45] Date of Patent: Aug. 3, 1993

[54] ENAMINE DERIVATIVES

[75] Inventors: Yasuo Katsuya; Takayuki Akimoto; Yoshii Morishita; Yasushi Shinbo; Akira Kageyama; Shigeru Hayashida, all of Hitachi, Japan

[73] Assignee: Hitachi, Ltd., Tokyo, Japan

[21] Appl. No.: 139,795

[22] Filed: Dec. 30, 1987

[30] Foreign Application Priority Data

Oct. 21, 1987 [JP] Japan .................... 62-265834

[51] Int. Cl.$^5$ ............................. C07C 211/49
[52] U.S. Cl. ........................ 564/319; 564/316; 564/431; 564/434; 564/383; 430/30
[58] Field of Search ............... 507/31 C, 431; 430/30; 564/319, 383, 434

[56] References Cited

U.S. PATENT DOCUMENTS 3,526,501 9/1970 Fox .................................. 564/433 X
3,677,752 7/1972 Looker et al. .................. 564/315 X

FOREIGN PATENT DOCUMENTS 2064481 7/1971 Fed. Rep. of Germany .
3414141 10/1984 Fed. Rep. of Germany .

OTHER PUBLICATIONS

Scheibe et al, Chemical Abstracts, vol. 66 (1967) 18444v.
Bredereck et al, Chemical Abstracts, vol. 72 (1970) 54695k.
Lavielle et al, Chemical Abstracts, vol. 73 (1970) 55579h.
Broekhof et al, Chemical Abstracts, vol. 102 (1984) 112475q.

Primary Examiner—Richard L. Raymond
Attorney, Agent, or Firm—Antonelli, Terry, Stout & Kraus

[57] ABSTRACT

A novel enamine derivative is effective as a charge transport material and can provide an electrophotographic plate excellent in sensitivity, photoresponse and durability.

12 Claims, 15 Drawing Sheets

ENAMINE DERIVATIVES

BACKGROUND OF THE INVENTION

This invention relates to enamine derivatives, processes for producing the same and electrophotographic plates containing the same as a charge transport material and excellent in sensitivity, photoresponse and durability.

In electrophotographic plates using photoconductive substances as a photosensitive material, there have been used mainly inorganic photoconductive substances such as selenium, zinc oxide, titanium oxide, cadmium sulfide, etc. But since most of these substances are generally strongly toxic, there is a problem in their disposal, otherwise they have low durability, e.g. in the case of zinc oxide.

On the other hand, photosensitive materials using organic photoconductive compounds are widely studied recently, since they are generally weak in toxicity and advantageous in transparency, flexibility, lightweight, cost, and the like comparing with the case of using the inorganic photoconductive substances.

Particularly in the case of two layers type electrophotographic plates wherein functions of generation and transport of charges are separated, the sensitivity which was a large defect of one layer type electrophotographic plates using organic photoconductive compounds can be improved greatly, so that the two layers type electrophotographic plates are rapidly progressing recently. These two layers type electrophotographic plates are applied to electrophotographic apparatuses by the Carlson method, e.g., copying machines, laser beam printers, facsimile machines, etc. With recent progress in miniaturization of electrophotographic apparatuses and high speed in printing speed, there have been demanded for electrophotographic plates so-called high speed photoresponse, wherein a surface potential at the time of exposing to a light image decays in a short time, and a longer life of printed copies.

The high speed photoresponse and the longer life are explained in detail below. With miniaturization of the electrophotographic apparatus, the diameter of a photoreceptive drum used in the apparatus becomes smaller. For example, the diameter of photosensitive drum in a large-size apparatus is 100 to 300 mm, while that in a small-size apparatus is 30 to 60 mm. Thus, in the small-size apparatus, individual parts such as a charging device, a developing device, etc. around the photoreceptive drum are installed in a narrow space and a time required for from the exposure to light image to the development is shortened compared with middle-size and large-size machines. Further, when the drum diameter is small, it is necessary to increase the revolving rate of drum in order to copy or print on sheets with the same rate. Therefore, in an electrophotographic process the time required for each step in an electrophotographic process of charging→exposing to a light image→developing→transferring→destaticizing becomes shorter and shorter. Further, among required performance for the electrophotographic plates, it becomes important to decay the surface potential rapidly after exposure to a light image. In other words, it is necessary to obtain electrophotographic plates good in photoresponse.

Further, since the drum diameter is reduced and the revolving rate is increased, it is necessary to repeat the above-mentioned electrophotographic process much more times compared with the case of using a larger drum diameter in order to obtain the same number of sheets by electrophotography. Thus, it is necessary to improve durability for repeated use of the electrophotographic plates.

The organic photosensitive body generally comprises a charge generating material which generates charges by absorbing light, a charge transport material which transports the charges, a binder and a small amount of additives depending on necessity. The photoresponse is mainly controlled by the charge transport material. In order to obtain high speed photoresponse, it is known to select suitable charge transport materials, or to increase the compounding ratio of the charge transport material to the binder.

As the charge transport materials, there are known pyrazoline derivatives disclosed in e.g. J. Photographic Science and Engineering vol. 21(2), p.73 (1977), etc.; oxazole derivatives disclosed in e.g. Japanese Patent Unexamined Publication No. 58-87557, U.S. Pat. Nos. 4,346,157; 4,619,879; 4,150,987; 4,278,747; 4,367,273; 4,365,014 and 4,454,212; hydrazone derivatives disclosed in e.g. Japanese Patent Unexamined Publication Nos. 54-59143, 54-150128 and 55-46760; enamine derivatives disclosed in e.g. J. Imaging Science vol. 29(1), p. 7 (1985); etc.

As to the method for enlarging the compounding ratio of the charge transport material to the binder in order to obtain high speed photoresponse, there are problems in known charge transport materials. For example, in the case of using pyrazoline derivatives and oxazole derivatives, the photoresponse is improved by increasing the compounding ratio of the charge transport material to the binder, but durability for repeated electrophotographic process is lowered, and there take place phenomena that an image fine line is broadened in the case of regular development and an image fine line is thinned in the case of reverse development. Such phenomena are called as lowering in print resolution. In the case of using hydrazone derivatives as the charge transport material, the photoresponse is undesirably slow, and there take place undesirably image fogging (toners are adhered to a white ground to make black) in the case of regular development and lowering in print density in the case of reverse development, due to an increase of potential after exposure to a light image, that is, an increase of residual potential, when electrophotography is repeated.

On the other hand, according to the above-mentioned J. Imaging Science, the following enamine derivatives are disclosed:

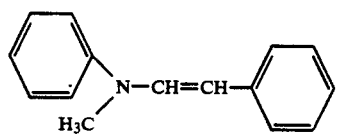

(A)

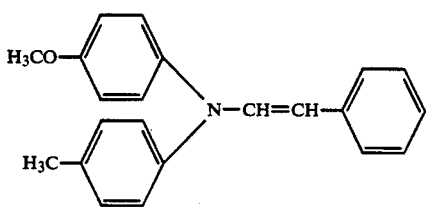

(B)

-continued

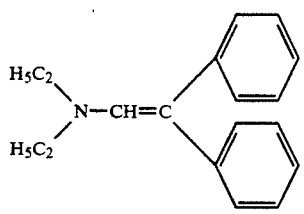

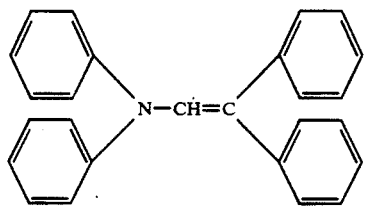

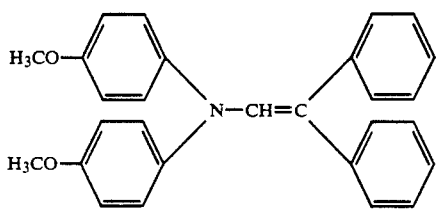

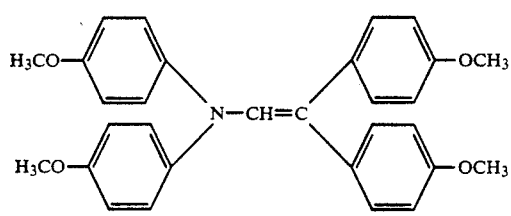

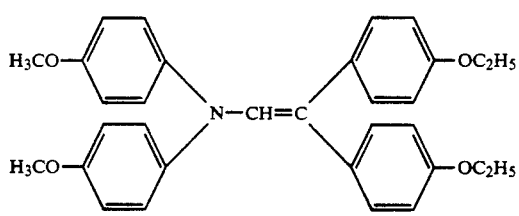

Among the compounds, it is described that the compounds (A), (B) and (C) are lacking in photoconductivity, the compound (D) is poor in photoconductivity and the compounds (E), (F) and (G) have good or excellent photoconductivity. But when the compounds (E), (F) and (G) are used as a charge transport material, they can withstand the repeated use but are insufficient in the sensitivity and photoresponse. The improvement in these points has been desired.

SUMMARY OF THE INVENTION

It is an object of this invention to provide enamine derivatives usable as a charge transport material excellent in photoresponse and durability in repeated use. It is another object of this invention to provide processes for producing these enamine derivatives. It is a further object of this invention to provide an electrophotographic plate containing such enamine derivatives as a charge transport material.

This invention provides an enamine derivative of the formula:

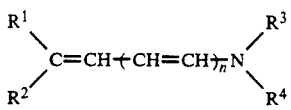

wherein (i) in the case of n being zero,
(a) $R^1$ is a group of the formula:

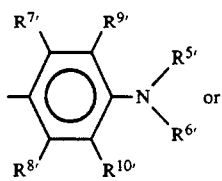

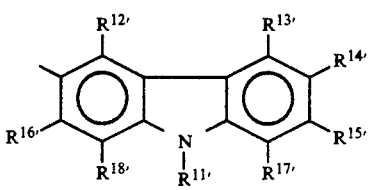

in which $R^{5'}$ and $R^{6'}$ are independently an alkyl group having 1 to 9 carbon atoms, an aryl group which may have one or more substituents, an aralkyl group which may have one or more substituents, or a heterocyclic ring group; $R^{7'}$ and $R^{8'}$ are independently hydrogen, an alkyl group having 1 to 9 carbon atoms, or an alkoxy group having 1 to 4 carbon atoms; $R^{9'}$ and $R^{10'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group, or a cyano group; $R^{11'}$ is an alkyl group having 1 to 9 carbon atoms, an aryl group which may have one or more substituents, an aralkyl group which may have one or more substituents, or a heterocyclic ring group; $R^{12'}$, $R^{13'}$, $R^{14'}$, $R^{15'}$ and $R^{16'}$ are independently hydrogen, an alkyl group having 1 to 9 carbon atoms, or an alkoxy group having 1 to 4 carbon atoms; $R^{17'}$ and $R^{18'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group; $R^2$, $R^3$ and $R^4$ are independently an alkyl group having 1 to 9 carbon atoms, an aryl group which may have one or more substituents, an aralkyl group which may have one or more substituents, or a heterocyclic ring group, and further $R^2$ may be hydrogen, and $R^3$ and $R^4$ may together form a group of the formula:

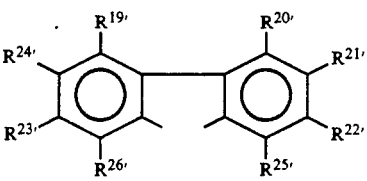

in which $R^{19'}$, $R^{20'}$, $R^{21'}$, $R^{22'}$, $R^{23'}$ and $R^{24'}$ are independently hydrogen, an alkyl group having 1 to 9 carbon atoms or an alkoxy group having 1 to 4 carbon atoms; $R^{25'}$ and $R^{26'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group, or (b) $R^1$ is a group of the formula:

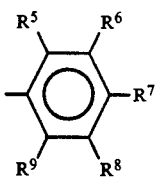

in which $R^5$, $R^6$, $R^7$, $R^8$ and $R^9$ are independently hydrogen, a halogen atom, a straight- or branched-chain, non-substituted or substituted alkyl group having 1 to 9 carbon atoms, a non-substituted or substituted aralkyl group, a straight- or branched-chain alkoxy group having 1 to 4 carbon atoms, a non-substituted or substituted aryloxy group, an amino group substituted with one or two straight- or branched-chain non-substituted or substituted alkyl groups having 1 to 9 carbon atoms, an amino group substituted with one or two non-substituted or substituted aralkyl groups, an amino group substituted with one or two non-substituted or substituted aryl groups, an amino group substituted with one or two non-substituted or substituted heterocyclic ring groups, a hydroxyl group, a nitro group or a cyano group; $R^2$ is hydrogen, an alkyl group having 1 to 9 carbon atoms, an aryl group which may have one or more substituents, an aralkyl group which may have one or more substituents, or a heterocyclic ring group; and $R^3$ and $R^4$ together forms a group of the formula:

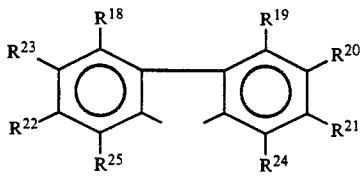

in which $R^{18}$, $R^{19}$, $R^{20}$, $R^{21}$, $R^{22}$ and $R^{23}$ are independently hydrogen, a straight- or branched-chain, non-substituted or substituted alkyl group having 1 to 9 carbon atoms, or an alkoxy group having 1 to 4 carbon atoms; $R^{24}$ and $R^{25}$ are independently hydrogen, a halogen atom, a straight-or branched-chain, non-substituted or substituted alkyl group having 1 to 9 carbon atoms, a non-substituted or substituted aralkyl group, an alkoxy group having 1 to 4 carbon atoms, a hydroxyl group, a nitro group or a cyano group; and (ii) in the case of n being an integer of 1 or 2, $R^1$ is a group of the formula:

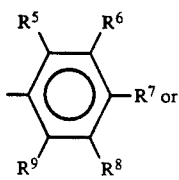

-continued

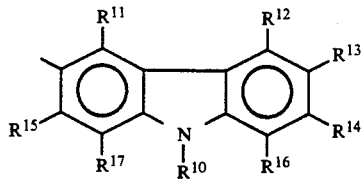

in which $R^5$ through $R^9$ are as defined above; is a straight- or branched-chain, non-substituted or substituted alkyl group having 1 to 9 carbon atoms, a non-substituted or substituted aryl group, a non-substituted or substituted aralkyl group, or a non-substituted or substituted heterocyclic ring group; $R^{11}$, $R^{12}$, $R^{13}$, $R^{14}$ and $R^{15}$ are independently hydrogen, a halogen atom, a straight- or branched-chain, non-substituted or substituted alkyl group having 1 to 9 carbon atoms, an alkoxy group having 1 to 4 carbon atoms, a non-substituted or substituted aralkyl group, a non-substituted or substituted aryl group, on a non-substituted or substituted heterocyclic ring group; $R^{16}$ and $R^{17}$ are independently hydrogen, a halogen atom, a straight- or branched-chain, non-substituted or substituted alkyl group having 1 to 9 carbon atoms, a non-substituted or substituted aralkyl group, an alkoxy group having 1 to 4 carbon atoms, a hydroxyl group, a nitro group, or a cyano group; $R^2$, $R^3$ and $R^4$ are independently a straight- or branched-chain, non-substituted or substituted alkyl group having 1 to 9 carbon atoms, a non-substituted or substituted aralkyl group, a non-substituted or substituted aryl group, or a non-substituted or substituted heterocyclic ring group, and further $R^2$ may be a hydrogen atom, and $R^3$ and $R^4$ may together form a group of the formula:

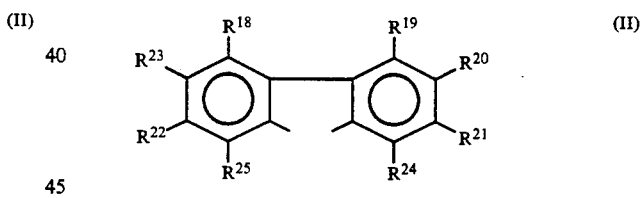

in which $R^{18}$ through $R^{25}$ are as defined above.

This invention also provides processes for producing the enamine derivative of the formula (I) variously.

This invention further provides an electrophotographic plate characterized by using the enamine derivative of the formula (I) as a charge transport material.

DESCRIPTION OF THE PREFERRED EMBODIMENTS

Figure 1:
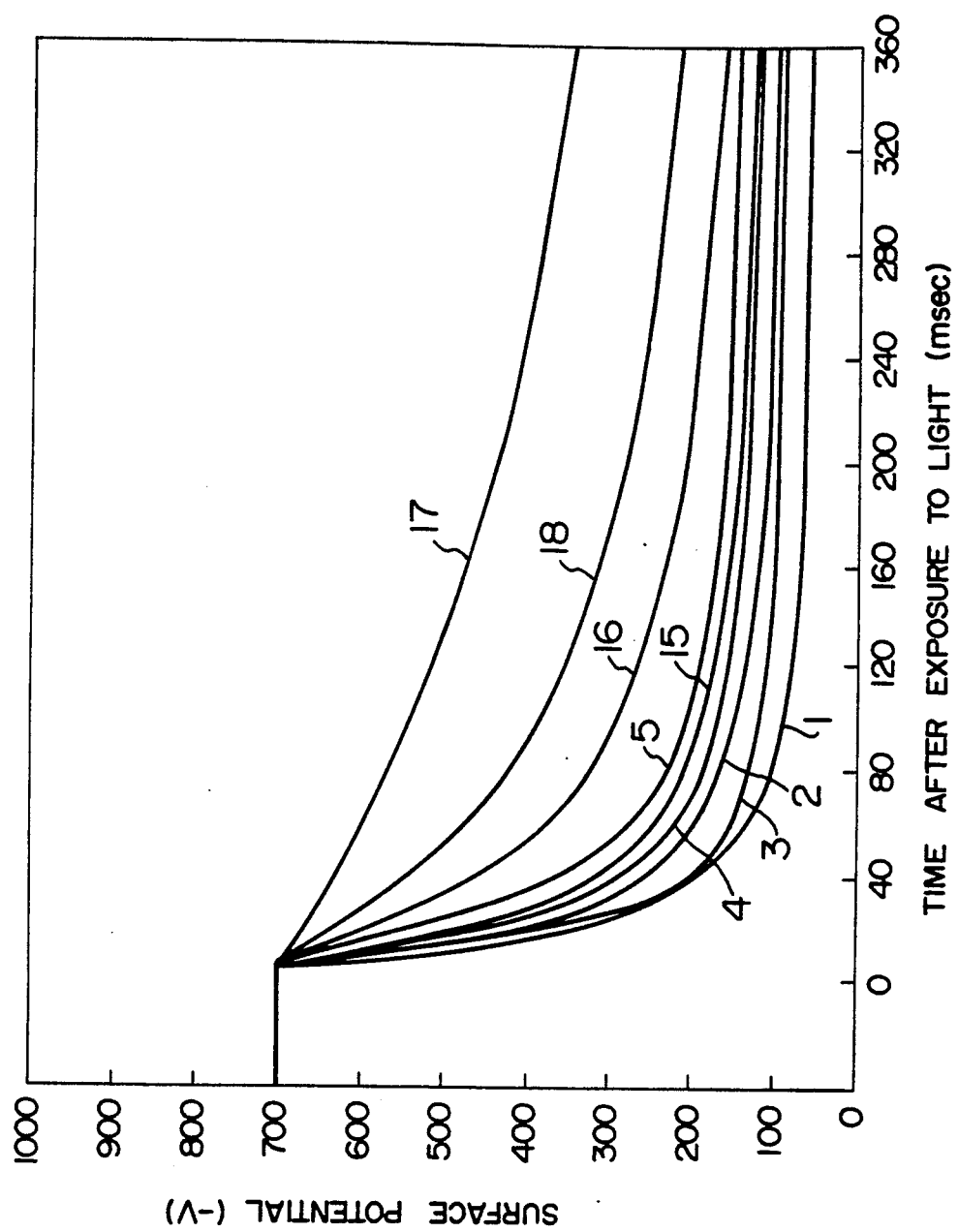
FIGS. 1 to 3 are graphs showing surface potential decaying curves obtained in the photoresponse test of eleotrophotographic plates of Examples and Comparative Examples.

The enamine derivative of this invention is represented by the formula:

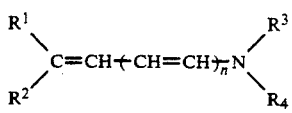 (I)

wherein (i) in the case of n being zero,
(a) $R^1$ is a group of the formula:

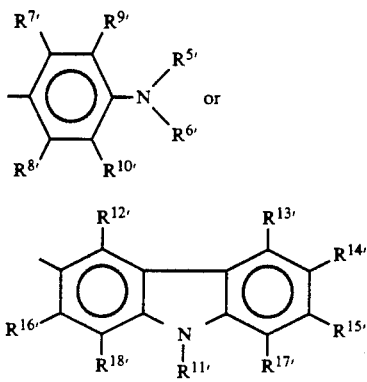

in which $R^{5'}$ and $R^{6'}$ are independently an alkyl group to 9 carbon atoms, an aryl group which may have one or more substituents, an aralkyl group which may have one or more substituents, or a heterocyclic ring group; $R^{7'}$ and $R^{8'}$ are independently hydrogen, an alkyl group having 1 to 9 carbon atoms, or an alkoxy group having 1 to 4 carbon atoms; $R^{9'}$ and $R^{10'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group, or a cyano group; $R^{11'}$ is an alkyl group having 1 to 9 carbon atoms, an aryl group which may have one or more substituents, an aralkyl group which may have one or more substituents, or a heterocyclic ring group; $R^{12'}$, $R^{13'}$, $R^{14'}$, $R^{15'}$ and $R^{16'}$ are independently hydrogen, an alkyl group having 1 to 9 carbon atoms, or an alkoxy group having 1 to 4 carbon atoms; $R^{17'}$ and $R^{18'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group; $R^2$, $R^3$ and $R^4$ are independently an alkyl group having 1 to 9 carbon atoms, an aryl group which may have one or more substituents, an aralkyl group which may have one or more substituents, or a heterocyclic ring group, and further $R^2$ may be hydrogen, and $R^3$ and $R^4$ may together form a group of the formula:

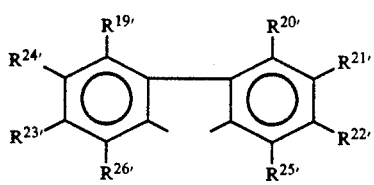

in which $R^{19'}$, $R^{20'}$, $R^{21'}$, $R^{22'}$, $R^{23'}$ and $R^{24'}$ are independently hydrogen, an alkyl group having 1 to 9 carbon atoms or an alkoxy group having 1 to 4 carbon atoms; $R^{25'}$ and $R^{26'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group, or (b) $R^1$ is a group of the formula:

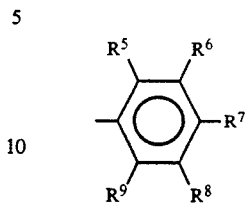

in which $R^5$, $R^6$, $R^7$, $R^8$ and $R^9$ are independently hydrogen, a halogen atom, a straight- or branched-chain, non-substituted or substituted alkyl group having 1 to 9 carbon atoms, a non-substituted or substituted aralkyl group, a straight- or branched-chain alkoxy group having 1 to 4 carbon atoms, a non-substituted or substituted aryloxy group, an amino group substituted with one or two straight- or branched-chain non-substituted or substituted alkyl groups having 1 to 9 carbon atoms, an amino group substituted with one or two non-substituted or substituted aralkyl groups, an amino group substituted with one or two non-substituted or substituted aryl groups, an amino group substituted with one or two non-substituted or substituted heterocyclic ring groups, a hydroxyl group, a nitro group or a cyano group; $R^2$ is hydrogen, an alkyl group having 1 to 9 carbon atoms, an aryl group which may have one or more substituents, an aralkyl group which may have one or more substituents, or a heterocyclic ring group; and $R^3$ and $R^4$ together forms a group of the formula:

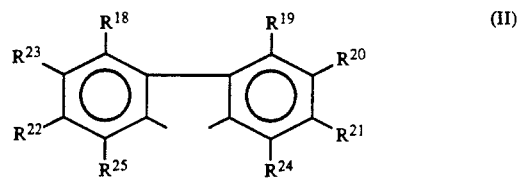 (II)

in which $R^{18}$, $R^{19}$, $R^{20}$, $R^{21}$, $R^{22}$ and $R^{23}$ are independently hydrogen, a straight- or branched-chain, non-substituted or substituted alkyl group having 1 to 9 carbon atoms, or an alkoxy group having 1 to 4 carbon atoms; $R^{24}$ and $R^{25}$ are independently hydrogen, a halogen atom, a straight-or branched-chain, non-substituted or substituted alkyl group having 1 to 9 carbon atoms, a non-substituted or substituted aralkyl group, an alkoxy group having 1 to 4 carbon atoms, a hydroxyl group, a nitro group or a cyano group; and (ii) in the case of n being an integer of 1 or 2, $R^1$ is a group of the formula:

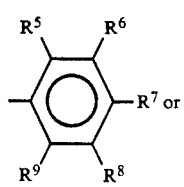 or

-continued

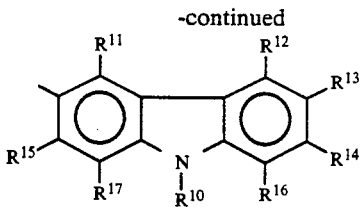

in which $R^5$ through $R^9$ are as defined above; $R^{10}$ is a straight- or branched-chain, non-substituted or substituted alkyl group having 1 to 9 carbon atoms, a non-substituted or substituted aryl group, a non-substituted or substituted aralkyl group, or a non-substituted or substituted heterocyclic ring group; $R^{11}$, $R^{12}$, $R^{13}$, $R^{14}$ and $R^{15}$ are independently hydrogen, a halogen atom, a straight- or branched-chain, non-substituted or substituted alkyl group having 1 to 9 carbon atoms, an alkoxy group having 1 to 4 carbon atoms, a non-substituted or substituted aralkyl group, a non-substituted or substituted aryl group, or a non-substituted or substituted heterocyclic ring group; $R^{16}$ and $R^{17}$ are independently hydrogen, a halogen atom, a straight- or branched-chain, non-substituted or substituted alkyl group having 1 to 9 carbon atoms, a non-substituted, or substituted aralkyl group, an alkoxy group having 1 to 4 carbon atoms, a hydroxyl group, a nitro group, or a cyano group; $R^2$, $R^3$ and $R^4$ are independently a straight- or branched-chain, non-substituted or substituted alkyl group having 1 to 9 carbon atoms, a non-substituted or substituted aralkyl group, a non-substituted or substituted aryl group, or a non-substituted or substituted heterocyclic ring group, and further $R^2$ may be a hydrogen atom, and $R^3$ and $R^4$ may together form a group of the formula:

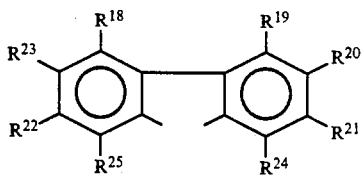

(II)

in which $R^{18}$ through $R^{25}$ are as defined above.

In the formulae (I) and (II), the straight- or branched-chain alkyl group having 1 to 9 carbon atoms includes a methyl group, an ethyl group, an n-propyl group, an isopropyl group, an n-butyl group, an isobutyl group, a sec-butyl group, a tert-butyl group, a pentyl group, a hexyl group, an octyl group, and a nonyl group. These alkyl groups may be substituted with one or more halogen atoms, hydroxyl groups, cyano groups, nitro groups, alkylamino groups, arylamino groups, aryl groups, aryloxy groups, etc. Examples of such substituted alkyl groups include a monochloromethyl group, a 1-hydroxyethyl group, an N,N-diphenylaminomethyl group, a 3-N,N-diethylaminobutyl group, a 2-cyanopentyl group, a 2-p-ethylphenoxyethyl group, etc.

The term "aryl group" includes a phenyl group, a biphenyl group, a xylyl group, a hydroxyphenyl group, a naphthyl group, an anthryl group, a phenanthryl group, and a pyrenyl group.

These aryl groups may be substituted with one or more halogen atoms, hydroxyl groups, cyano groups, nitro groups, alkylamino groups, amino groups, alkyl groups, alkoxy group, acetyl groups, acetoxy groups, arylamino and aralkylamino groups such as diphenylamino, ditolylamino, naphthylamino, di(m-methylphenyl)-amino, di(n-ethylphenyl)amino, di(p-methylphenyl)-amino, di(p-ethylphenyl)amino, dibenzylamino, diphenethylamino, di(p-methoxy)benzylamino, di(p-ethoxy)-benzylamino, di(m-methoxy)-benzylamino, and di(m-ethoxy)benzylamino; aryl groups such as phenyl, naphthyl, p-methoxyphenyl, p-ethoxyphenyl, p-dimethylaminophenyl, p-diethylaminophenyl, and p-di-tert-butylaminophenyl; aryloxy groups such as phenoxy, naphthoxy, anthryl, anthryloxy, p-methoxyphenyloxy, p-ethoxyphenyloxy, p-dimethylaminophenyloxy, p-diethylaminophenyloxy, and p-dimethylaminophenyloxy, p-diethylaminophenyloxy, and p-di-tert-butylaminophenyloxy groups.

Examples of substituted aryl groups are a hydroxyphenyl groups, a tolyl group, a xylyl group, a chlorophenyl group, a dimethylamino group, a diphenylamino group, a dibenzylaminophenyl group, a dianthrylaminophenyl group, etc.

The term "aryloxy group" includes a phenoxy group, a naphthoxy group, a tolyloxy group, a biphenyloxy group, a xylyloxy group, a hydroxyphenyloxy group, a naphthyloxy group, an anthryloxy group, a phenantryloxy group, and a pyrenyloxy group.

These aryloxy groups may be substituted with one or more halogen atoms, hydroxyl groups, cyano groups, nitro groups, alkylamino groups, amino groups, alkyl groups, alkoxy groups, acetyl groups, acetoxy groups, the same arylamino groups, aralkylamino groups, aryl groups, aryloxy groups, as mentioned above, etc.

Examples of substituted aryloxy groups are a chlorophenyloxy group, a hydroxyphenyloxy group, a tolyloxy group, a xylyloxy group, a dimethylaminophenyloxy group, a diphenylaminophenyloxy group, a dibenzylaminophenyloxy group, a dianthrylaminophenyloxy group, a 3-methylnaphthyloxy group, etc.

The term "aralkyl group" includes a benzyl group, a phenylethyl group, a naphthylethyl group, a naphthylmethyl group, etc.

These aralkyl groups may be substituted with one or more halogen atoms, hydroxyl groups, cyano groups, nitro groups, alkylamino groups, amino groups, alkyl groups, alkoxy groups, acetyl groups, acetoxy groups, the same aryl groups, aryloxy groups, arylamino groups, aralkylamino groups as mentioned above, etc.

Examples of substituted aralkyl groups are a diethylaminobenzyl group, a 3-hydroxyphenyl group, a p-ethoxy-o-chlorobenzyl group, etc.

The term "heterocyclic ring group" includes a furyl group, a thiofuryl group, a pyrrolyl group, a pyranyl group, a pyridyl group, an oxazolyl group, a thiazolyl group, a pyrimidinyl group, a triazolyl group, an acridinyl group, a carbazolyl group, a carbolinyl group, a quinolyl group, a phenothiazinyl group, a quinoxalinyl group, a pyrazolinyl group, an imidazolyl group, an oxadiazolyl group, an indolyl group, etc.

These heterocyclic ring groups may be substituted with one or more halogen atoms, hydroxyl groups, cyano groups, nitro groups, alkylamino groups, amino groups, alkyl groups, alkoxy groups, acetyl groups, acetoxy groups, the same aryl groups, aryloxy groups, arylamino groups, aralkylamino groups as mentioned above, etc.

Examples of substituted heterocyclic ring groups are a 2-methylpyrrolyl group, a 3-p-dimethylphenyl-1,3-oxazolyl group, a 4-ethylcarbazolyl group, etc.

The straight- or branched-chain alkoxy group having 1 to 4 carbon atoms includes a methoxy group, an ethoxy group, a propoxy group, an isopropoxy group, a butoxy group, a sec-butoxy group, a tert-butoxy group, etc.

The amino group substituted with one or two straight- or branched-chain, non-substituted or substituted alkyl groups having 1 to 9 carbon atoms includes a monomethylamino group, a dimethylamino group, a diethylamino group, a monoisopropylamino group, etc.

The amino group substituted with one or two non-substituted or substituted aralkyl groups includes a monobenzylamino group, a dibenzylamino group, a monophenylethylamino group, a di(phenylethyl)amino group, a monomethylbenzylamino group, a di(methylbenzyl)amino group, etc.

The amino group substituted with one or two non-substituted or substituted aryl groups includes a monophenylamino group, a diphenylamino group, a monotolylamino group, a ditolylamino group, a mononaphthylamino group, a dinaphthylamino group, etc.

The amino group substituted with one or two non-substituted or substituted heterocyclic ring groups includes a monopyridylamino group, a dipyridylamino group, a monoquinolylamino group, a diquinolylamino group, a monocarbazolylamino group, a dicarbazolylamino group, a monoacridinylamino group, a diacridinylamino group, a monooxazolylamino group, a dioxazolylamino group, etc.

The enamine derivatives of the formula (I) include those of the formula:

(I-1)

wherein $R^1$ is a group of the formula:

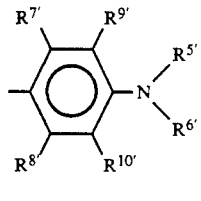

or

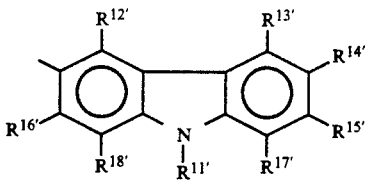

in which $R^{5'}$ and $R^{6'}$ are independently an alkyl group having 1 to 9 carbon atoms, an aryl group which may have one or more substituents, an aralkyl group which may have one or more substituents, or a heterocyclic ring group; $R^{7'}$ and $R^{8'}$ are independently hydrogen, an alkyl group having 1 to 9 carbon atoms, or an alkoxy group having 1 to 4 carbon atoms; $R^{9'}$ and $R^{10'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group, or a cyano group; $R^{11'}$ is an alkyl group having 1 to 9 carbon atoms, an aryl group which may have one or more substituents, an aralkyl group which may have one or more substituents, or a heterocyclic ring group; $R^{12'}$, $R^{13'}$, $R^{14'}$, $R^{15'}$ and $R^{16'}$ are independently hydrogen, an alkyl group having 1 to 9 carbon atoms, or an alkoxy group having 1 to 4 carbon atoms; $R^{17'}$ and $R^{18'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group; $R^2$, $R^3$ and $R^4$ are independently an alkyl group having 1 to 9 carbon atoms, an aryl group which may have one or more substituents, an aralkyl group which may have one or more substituents, or a heterocyclic ring group, and further $R^2$ may be hydrogen, and $R^3$ and $R^4$ may together form a group of the formula:

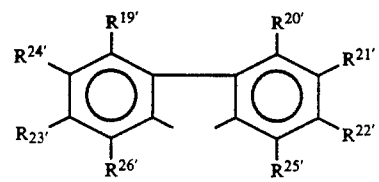

in which $R^{19'}$, $R^{20'}$, $R^{21'}$, $R^{22'}$, $R^{23'}$ and $R^{24'}$ are independently hydrogen, an alkyl group having 1 to 9 carbon atoms or an alkoxy group having 1 to 4 carbon atoms; $R^{25'}$ and $R^{26'}$ are independently hydrogen, a halogen atom, an alkyl group having 1 to 9 carbon atoms, an alkoxy group having 1 to 4 carbon atoms, an aralkyl group which may have one or more substituents, a hydroxyl group, a nitro group or a cyano group.

The enamine derivatives of the formula (I) include those of the formula:

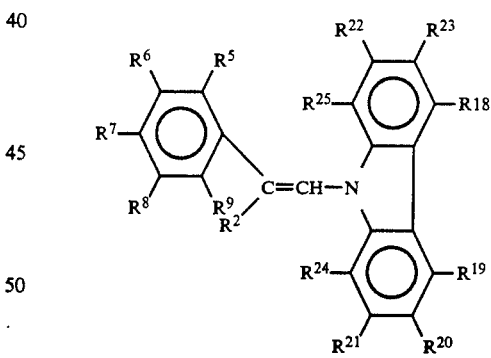

wherein $R^5$ through $R^9$ and $R^{18}$ through $R^{25}$ are as defined above; and $R^2$ is hydrogen, an alkyl group having 1 to 9 carbon atoms, an aryl group which may have one or more substituents, an aralkyl group which may have one or more substituents, or a heterocyclic ring group.

The enamine derivatives of the formula (I) include those of the formula:

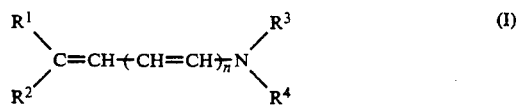

(I)

wherein $R^1$ is a group of the formula:

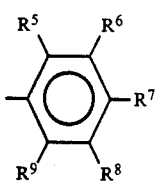

or

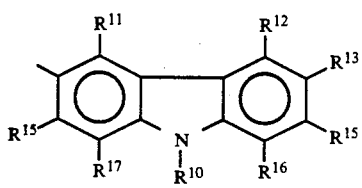

in which $R^5$, $R^6$, $R^7$, $R^8$ and $R^9$ are independently hydrogen, a halogen atom, a straight- or branched-chain, non-substituted or substituted alkyl group having 1 to 9 carbon atoms, a non-substituted or substituted aralkyl group, a straight- or branched-chain alkoxy group having 1 to 4 carbon atoms, a non-substituted or substituted aryloxy group, an amino group substituted with one or two straight- or branched-chain alkyl groups having 1 to 9 carbon atoms, an amino group substituted with one or two non-substituted or substituted aryl groups, a hydroxyl group, a nitro group or a cyano group; $R^{10}$ is a straight- or branched-chain, non-substituted or substituted alkyl group having 1 to 9 carbon atoms, a non-substituted or substituted aryl group, a non-substituted or substituted aralkyl group, or a non-substituted or substituted heterocyclic ring group; $R^{11}$, $R^{12}$, $R^{13}$, $R^{14}$ and $R^{15}$ are independently hydrogen, a halogen atom, a straight- or branched-chain, non-substituted or substituted alkyl group having 1 to 9 carbon atoms, a non-substituted or substituted aralkyl group, a non-substituted or substituted aryl group, or a non-substituted or substituted heterocyclic ring group; $R^{16}$ and $R^{17}$ are independently hydrogen, a straight- or branched-chain, non-substituted or substituted alkyl group having 1 to 9 carbon atoms, a non-substituted or substituted aralkyl group, an alkoxy group having 1 to 4 carbon atoms, a hydroxyl group, a nitro group, or a cyano group; $R^2$, $R^3$ and $R^4$ are independently a straight- or branched-chain, non-substituted or substituted alkyl group having 1 to 9 carbon atoms, a non-substituted or substituted aralkyl group, a non-substituted or substituted aryl group, or a non-substituted or substituted heterocyclic ring group, and further $R^2$ may be a hydrogen atom, and $R^3$ and $R^4$ may together form a group of the formula:

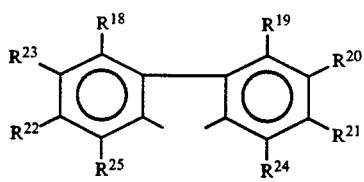

(II)

in which $R^{18}$, $R^{19}$, $R^{20}$, $R^{21}$, $R^{22}$ and $R^{23}$ are independently hydrogen, a straight- or branched-chain, non-substituted or substituted alkyl group having 1 to 9 carbon atoms, or an alkoxy group having 1 to 4 carbon atoms; $R^{24}$ and $R^{25}$ are independently hydrogen, a halogen atom, a straight- or branched-chain, non-substituted or substituted alkyl group having 1 to 9 carbon atoms, a non-substituted or substituted aralkyl group, an alkoxy group having 1 to 4 carbon atoms, a hydroxyl group, a nitro group or a cyano group; and n is an integer of 1 or 2.

The enamine derivative of the formula (I) functions as a charge transport material. By using the enamine derivative of the formula (I) as a charge transport material, there can be obtained an electrophotographic plate excellent in photoresponse and durability in repeated use.

Among the enamine derivatives of the formula (I), preferable ones are those having as $R^1$ a group of the formula:

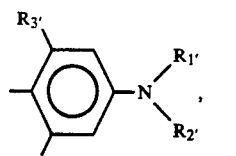

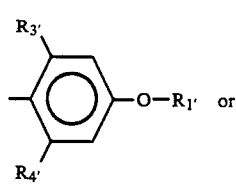

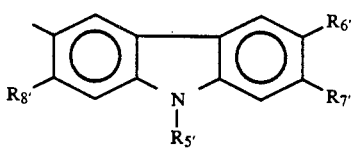

wherein $R_1'$ and $R_2'$ are independently a straight- or branched-chain alkyl group having 1 to b 4 carbon atoms, a group of the formula:

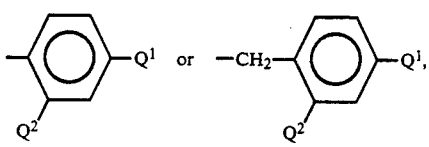

in which $Q^1$ and $Q^2$ are independently hydrogen, a straight- or branched-chain alkyl group having 1 to 4 carbon atoms, or a straight- or branched-chain alkoxy group having 1 to 4 alkoxy group; $R_5'$ is a straight- or branched-chain alkyl group having 1 to 4 carbon atoms or a phenyl group; $R_3'$, $R_4'$, $R_6'$, $R_7'$ and $R_8'$ are independently hydrogen, a straight- or branched-chain alkyl group having 1 to 4 carbon atoms, an alkoxy group having 1 to 4 carbon atoms, or a halogen atom; as $R^2$ hydrogen, a straight- or branched-chain alkyl group having 1 to 4 carbon atoms or a group of the formula:

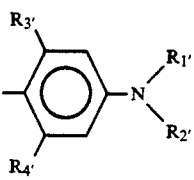

or

-continued

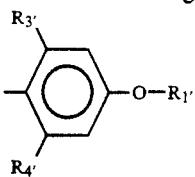

in which $R_1'$, $R_2'$, $R_3'$ and $R_4'$ are as defined above; as $R^3$ and $R^4$ independently a group of the formula:

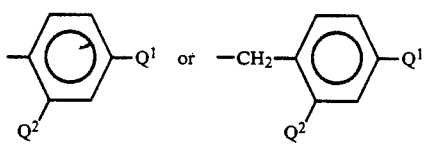

in which $Q^1$ and $Q^2$ are as defined above, or $R^4$ is an alkyl group having 1 to 4 carbon atoms, or $R^3$ and $R^4$ together form a group of the formula:

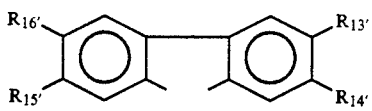

in which $R_{13}'$, $R_{14}'$, $R_{15}'$ and $R_{16}'$ are independently hydrogen, a straight- or branched-chain alkyl group having 1 to 4 carbon atoms, an alkoxy group having 1 to 4 carbon atoms, or a halogen atom; and n being zero or an integer of 1 or 2.

Particularly preferable enamine derivatives of the formula (I) are those having as $R^1$ the groups mentioned above and as $R^3$ the groups mentioned above.

More concretely, preferable substituents as $R^1$, $R^2$, $R^3$ and $R^4$ in the formula (I) are as follows:

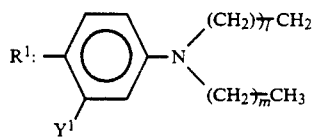

l = 0, 1, 2, or 3
m = 0, 1, 2, or 3
$Y^1$ = hydrogen, methoxy or ethoxy

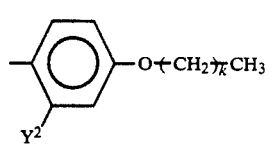

k = o, 1, 2, or 3
$Y^2$ = hydrogen, methoxy, or ethoxy

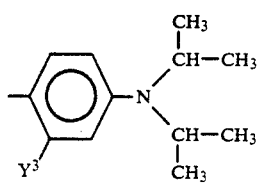

$Y^3$ = hydrogen, methoxy or ethoxy

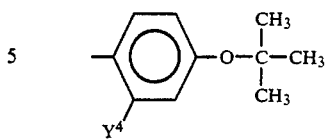

$Y^4$ = hydrogen, methoxy, or ethoxy

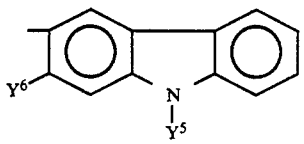

$Y^5$ = methyl or ethyl
$Y^6$ = hydrogen, or $C_{1-4}$ alkoxy
$R^2$: hydrogen, methyl, ethyl or

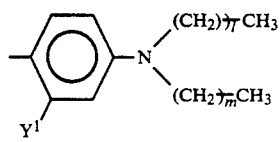

l, m, $Y^1$ = as defined above

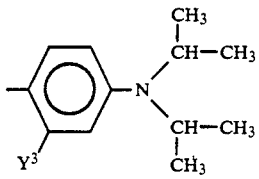

K, $Y^2$ = as defined above

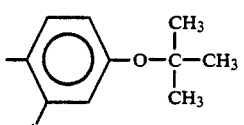

$Y^3$ = as defined above

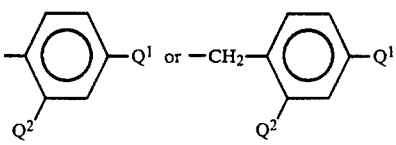

$Y^4$ = as defined above
$R^3$ and $R^4$ independently

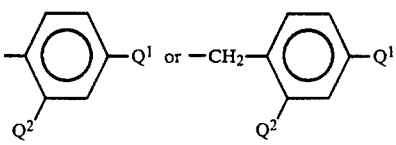

$Q^1$, $Q^2$ = as defined above
In combination to form

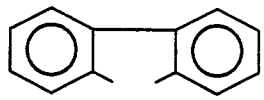
n: zero or an integer of 1 or 2
Examples of the enamine derivatives of the formula (I) are as follows:
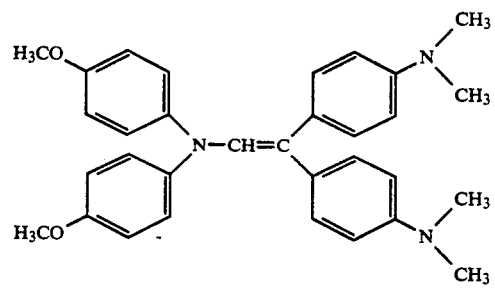
Compound 1
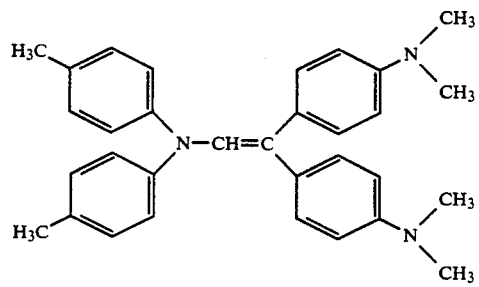
Compound 2
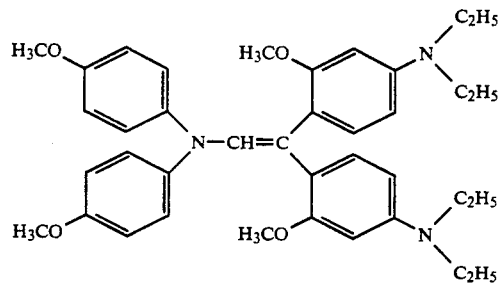
Compound 3
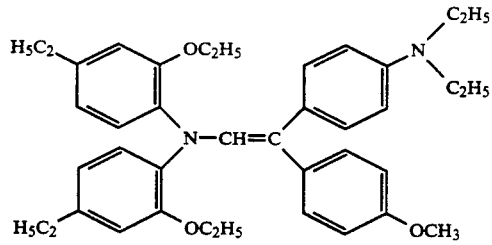
Compound 4
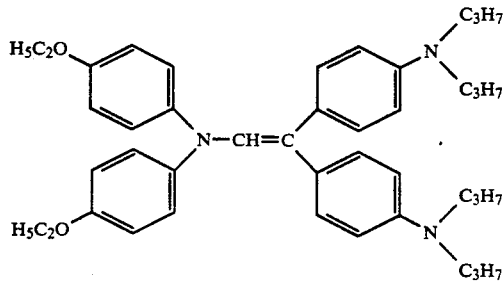
Compound 5

-continued
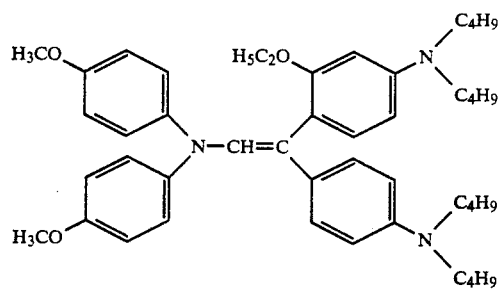
Compound 6
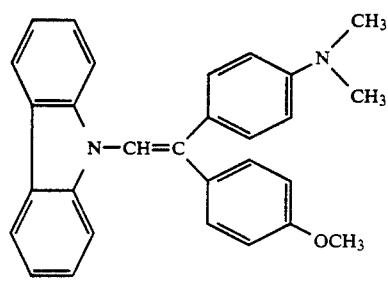
Compound 7
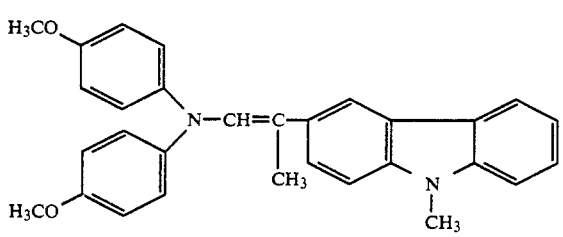
Compound 8
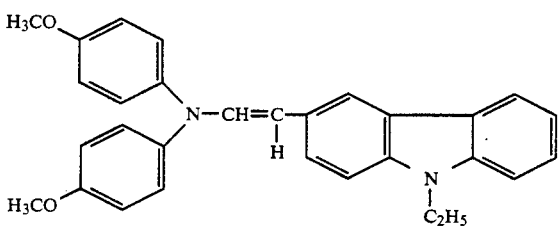
Compound 9
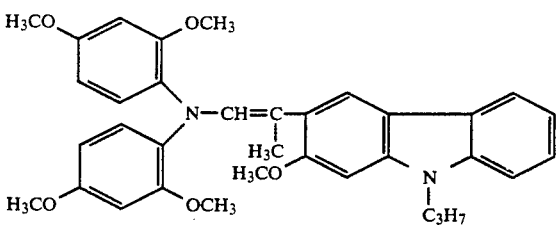
Compound 10
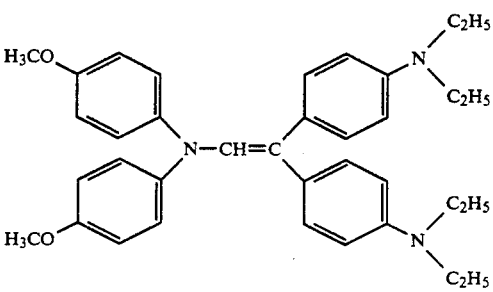
Compound 11

-continued
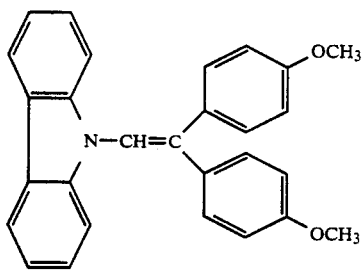
Compound 12
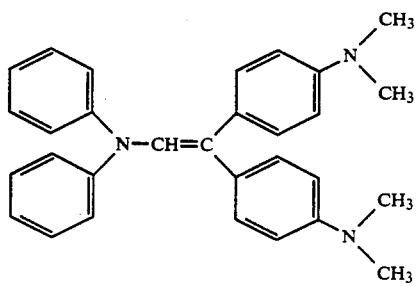
Compound 13
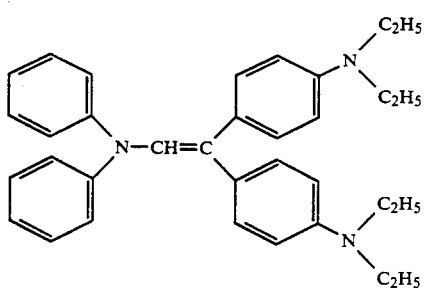
Compound 14
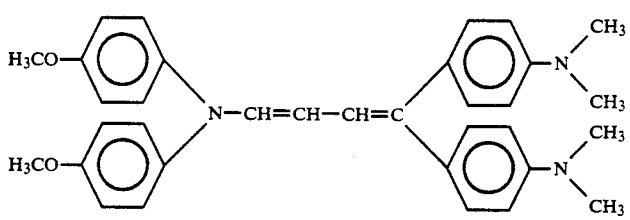
Compound 15
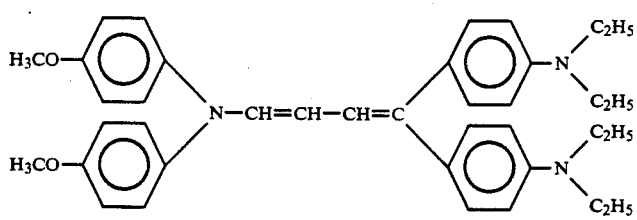
Compound 16
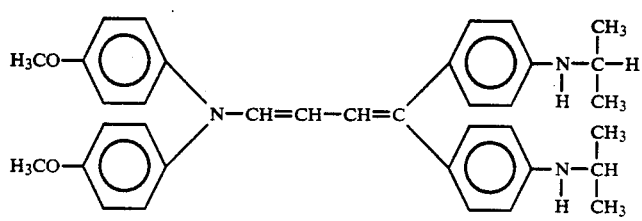
Compound 17

-continued
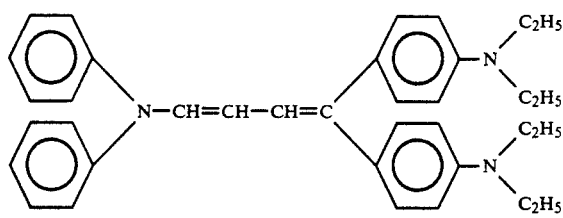
Compound 18
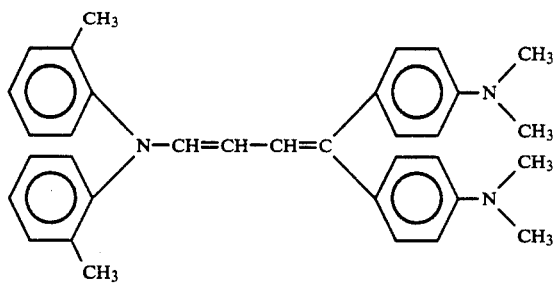
Compound 19
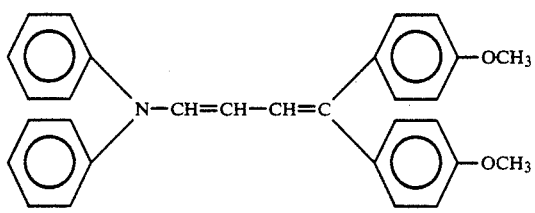
Compound 20
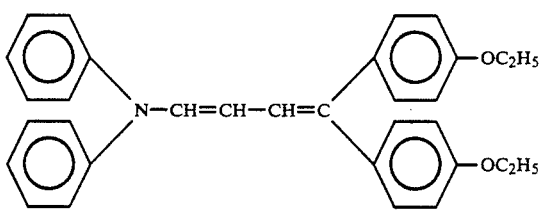
Compound 21
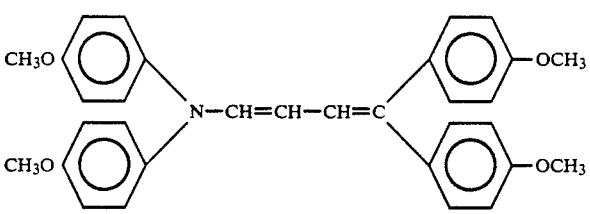
Compound 22
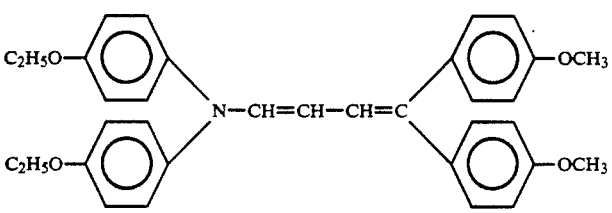
Compound 23
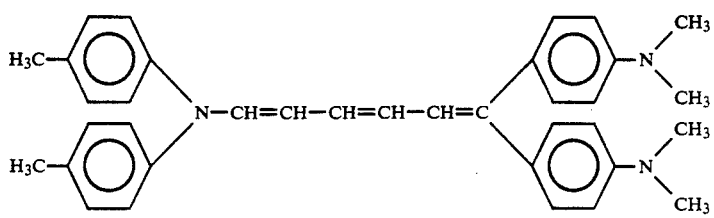
Compound 24

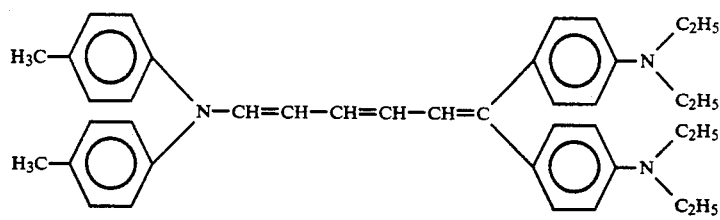
Compound 25
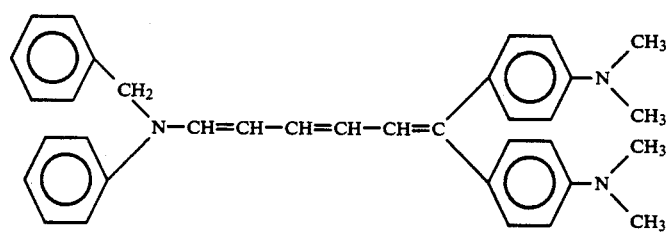
Compound 26
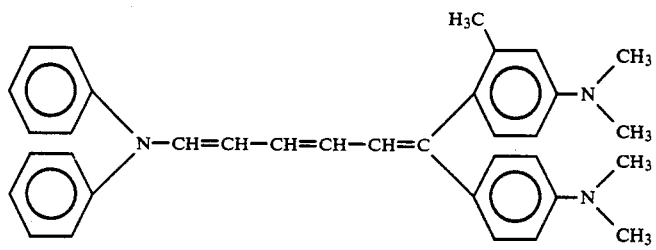
Compound 27
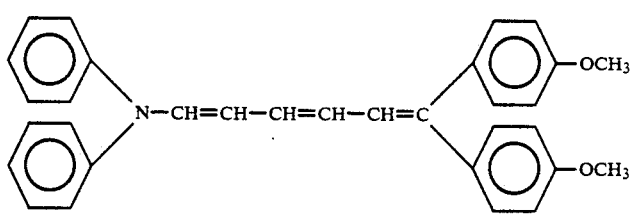
Compound 28
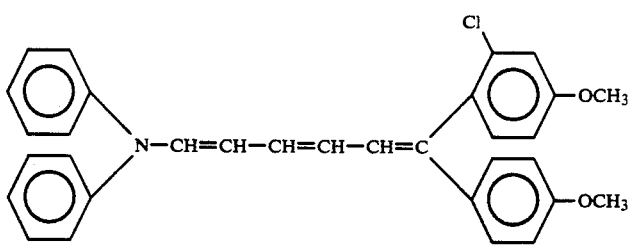
Compound 29
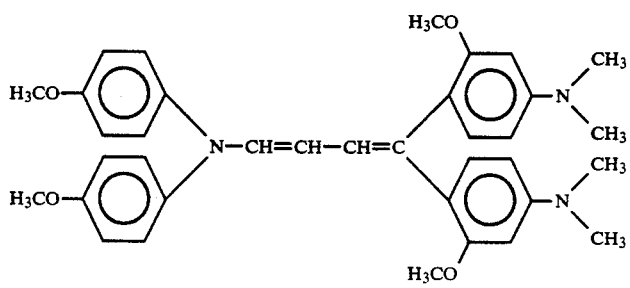
Compound 30

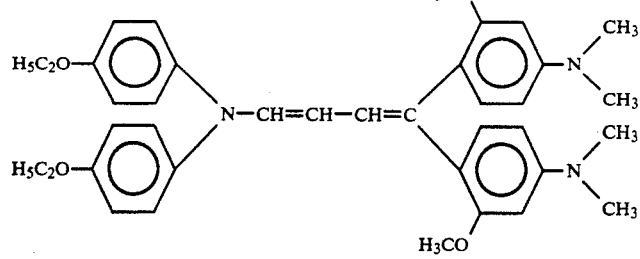
Compound 31
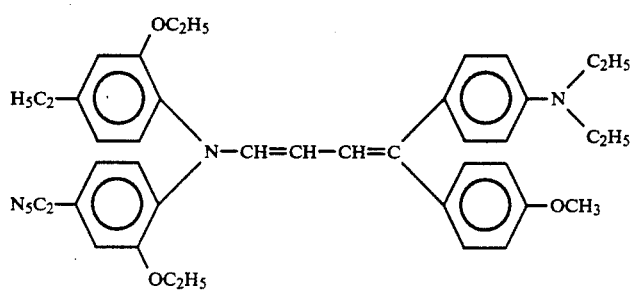
Compound 32
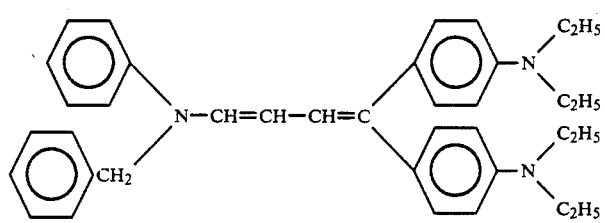
Compound 33
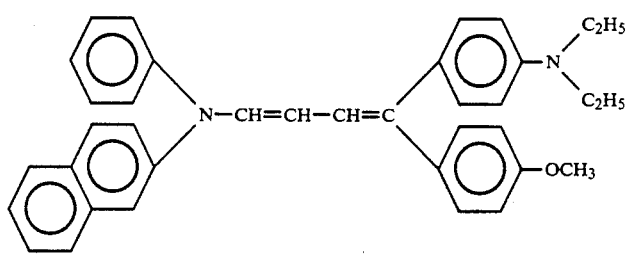
Compound 34
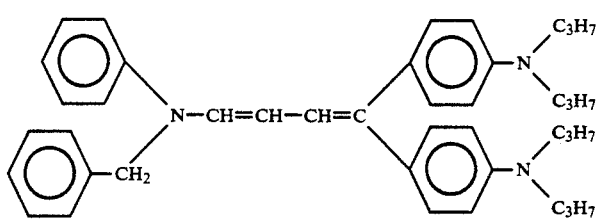
Compound 35
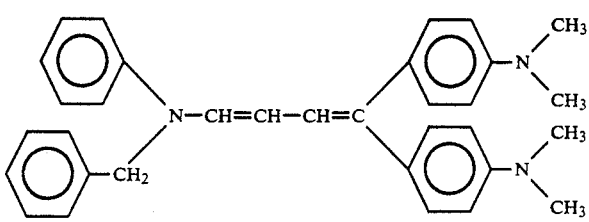
Compound 36

-continued
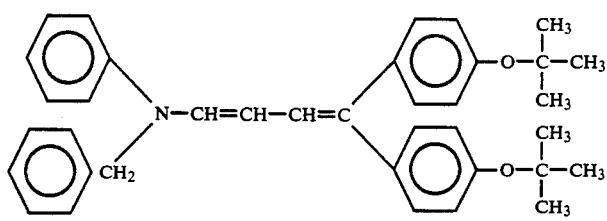
Compound 37
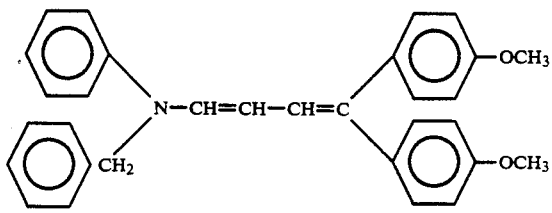
Compound 38
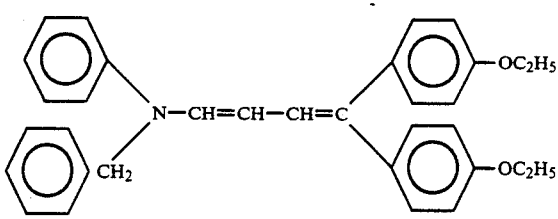
Compound 39
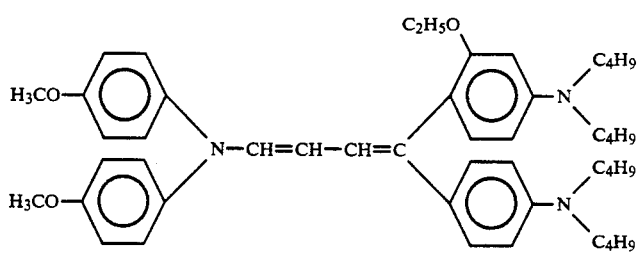
Compound 40
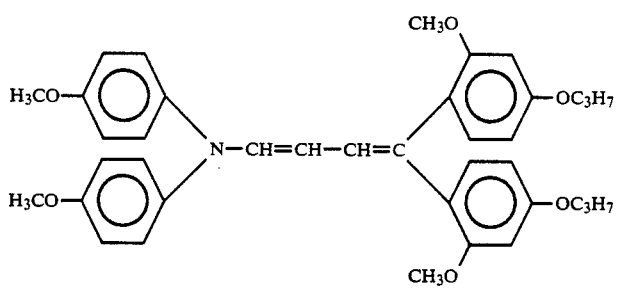
Compound 41
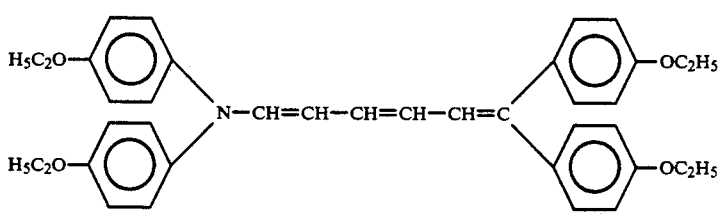
Compound 42
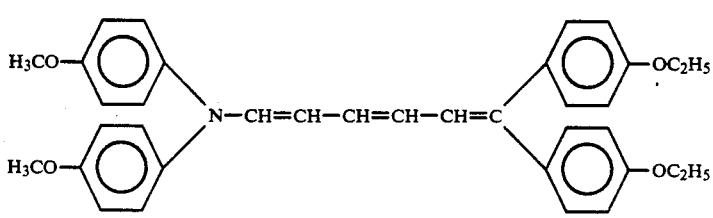
Compound 43

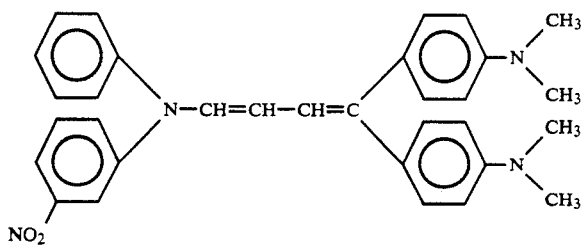
Compound 44
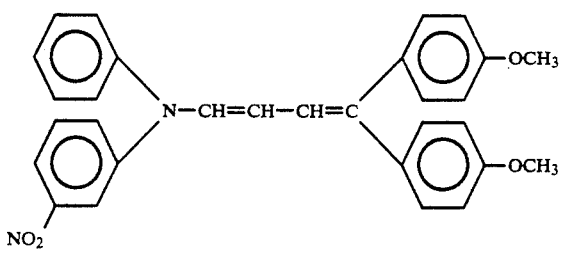
Compound 45
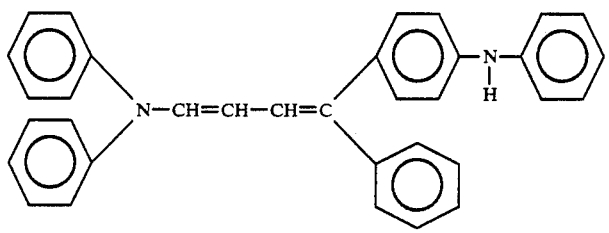
Compound 46
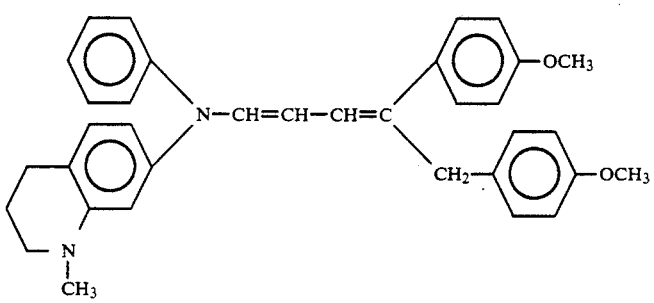
Compound 47
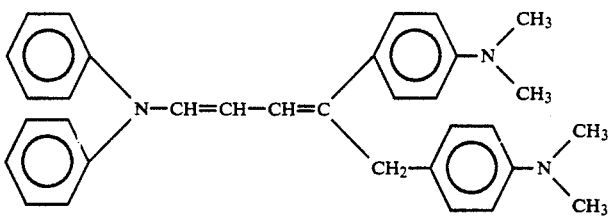
Compound 48
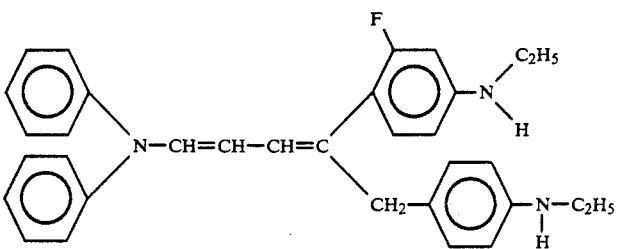
Compound 49

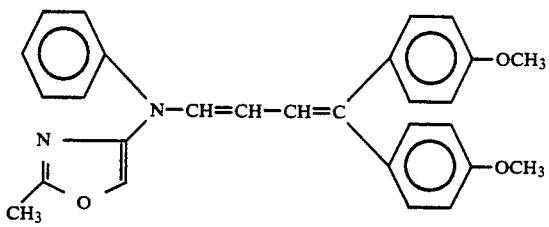
Compound 50
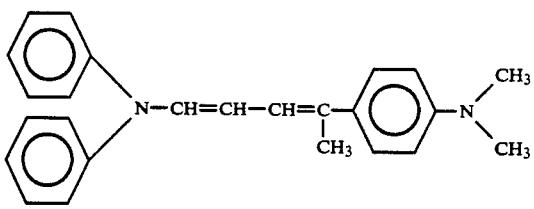
Compound 51
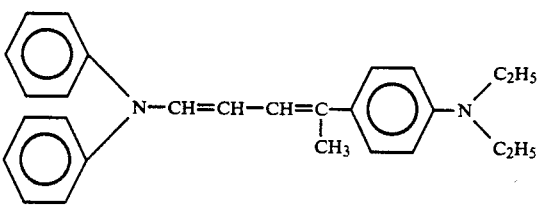
Compound 52
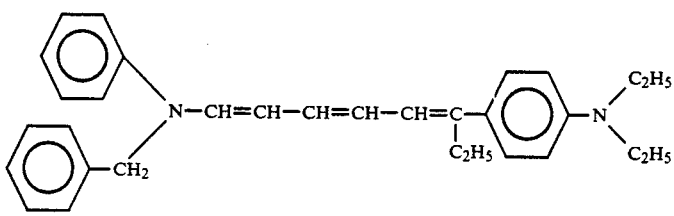
Compound 53
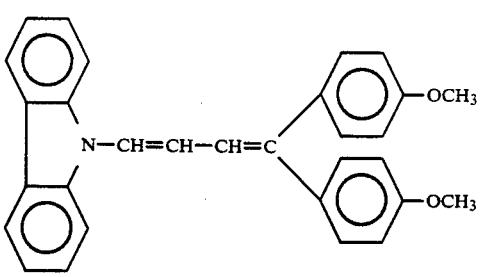
Compound 54
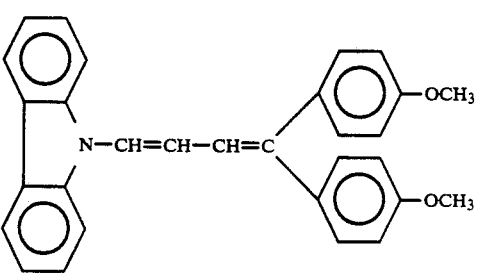
Compound 55

Compound 56
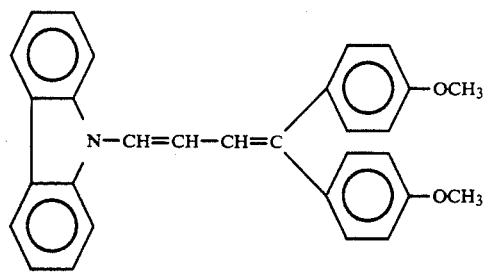
Compound 57
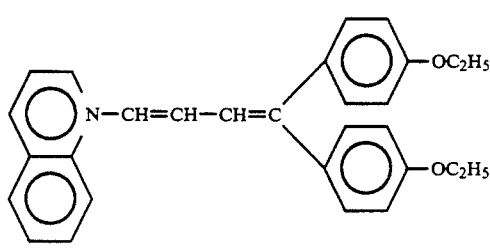
Compound 58
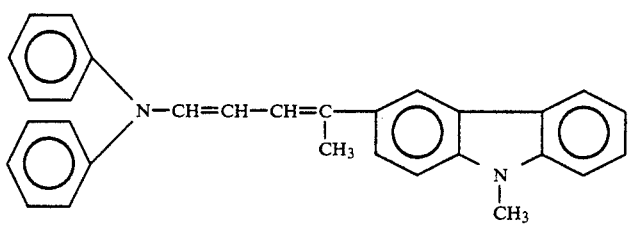
Compound 59
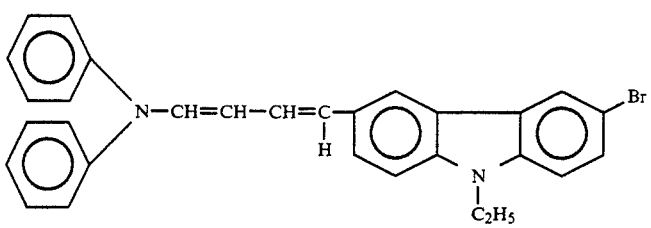
Compound 60
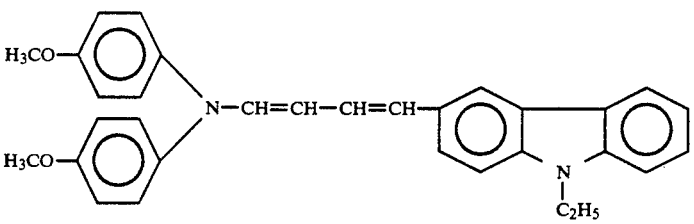
Compound 61
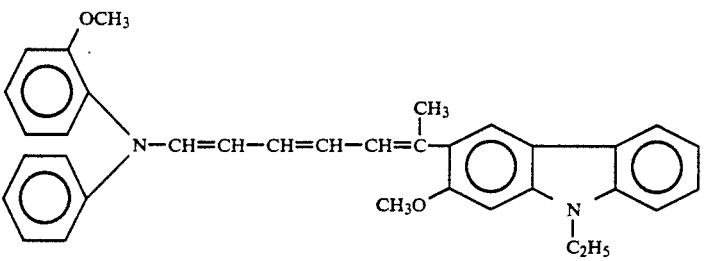

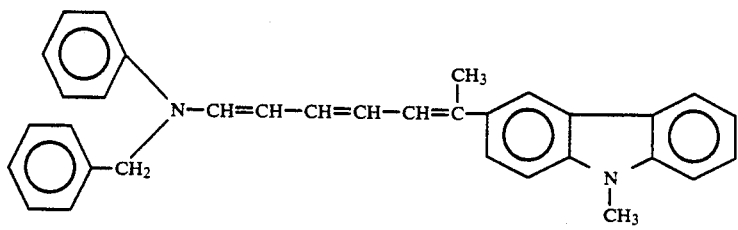

Compound 62

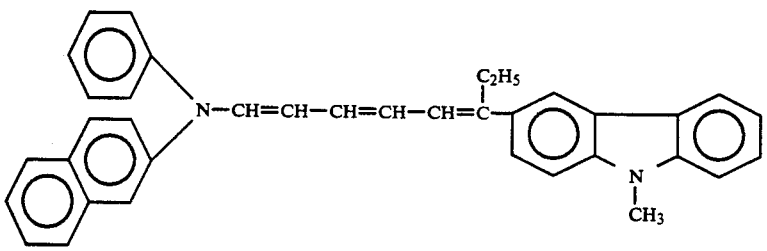

Compound 63

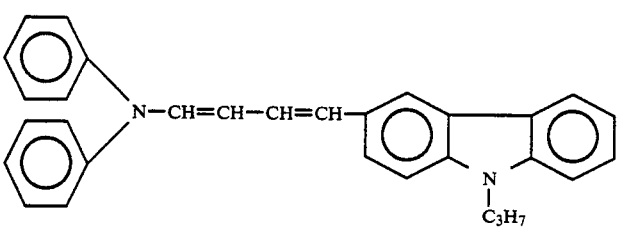

Compound 64

The compounds of the formula (I) can be produced by the processes A to D.

PROCESS A

Particularly, the compound of the formula:

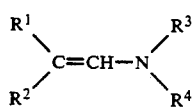
(I-1)

wherein $R^1$, $R^2$, $R^3$ and $R^4$ are as defined above, can be produced by reacting a compound of the formula:

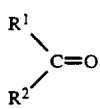
(III)

wherein $R^1$ and $R^2$ are as defined above, with a compound of the formula:

$$Ph_3P^{+-}ClCH_2OCH_3 \quad (IV-1)$$

wherein Ph is a phenyl group, in a solvent in the presence of an alkoxide or an organometallic compound to yield a compound of the formula:

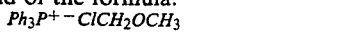
(V)

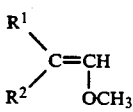

wherein $R^1$ and $R^2$ are as defined above, hydrolyzing the compound of the formula (V) with an acid, followed by alkali treatment to yield a compound of the formula:

(VI)

wherein $R^1$ and $R^2$ are as defined above, and reacting the compound of the formula (VI) with a compound of the formula:

(VII)

wherein $R^3$ and $R^4$ are as defined above, in a solvent in the presence of a sulfonic acid.

The reaction of the compound of the formula (III) with the compound of the formula (IV-1) is known as the Wittig reaction and carried out in a solvent in the presence of an alkoxide or an organometallic compound. As the solvent, there can be used tetrahydrofuran, dimethylformamide, etc. As the alkoxide, there can be used sodium methoxide, sodium ethoxide, potassium methoxide, potassium ethoxide, etc. As the organometallic compound, there can be used n-butyllithium, phenyllithium, etc. The reaction is preferably carried out at −20° C. to 50° C. for 30 minutes to 10 hours. The compound of the formula (V) is obtained by pouring the reaction mixture into a large amount of water, extracting with benzene or the like, removing the benzene or the like by distillation after dried, and purifying the residue by a silica gel column or the like.

The compound of the formula (V) is then hydrolyzed with an acid, followed by an alkali treatment to yield the compound of the formula (VI). As the acid, there can be used perchloric acid, hydrochloric acid, sulfuric acid, nitric acid, hydrobromic acid, hydroiodic acid, etc. The hydrolysis reaction can be carried out by dissolving the compound of the formula (V) in an acid with stirring preferably at 0° to 50° C. for 5 minutes to 2 hours. As the alkali used for the alkali treatment, there can be used sodium hydroxide, potassium hydroxide, sodium carbonate, potassium carbonate, etc. The alkali treatment is carried out at −20° C. to 30° C. The compound of the formula (VI) is obtained by extracting the reaction mixture with benzene or the like, removing the benzene or the like by distillation after dried to yield a crude product, which is recrystallized from methanol or the like.

The compound of the formula (VI) is then reacted with the compound of the formula (VII) in a solvent in the presence of a sulfonic acid. As the solvent, there can be used benzene, toluene, xylene, chlorobenzene, dichlorobenzene, etc. As the sulfonic acid, there can be used p-toluenesulfonic acid, benzenesulfonic acid, sulfuric acid, etc. Since the reaction is a dehydration reaction, the reaction can be carried out by removing the water from the reaction system placing molecular sieves 4A in the reaction system. The compound of the formula (VI) and the compound of the formula (VII) are used in almost equimolar amounts. The reaction can be carried out preferably at 50 to 130° C. for 30 minutes to 5 hours. The desired compound of the formula (I-1) can be obtained by removing the solvent from the reaction mixture by distillation to give a crude product, which is recrystallized from a suitable solvent such as isopropyl ether, or the like.

PROCESS B

The compound of the formula (I-1) can also be produced by reducing a compound of the formula:

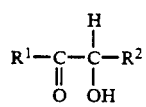
(VIII)

wherein $R^1$ and $R^2$ are as defined above, with a metal hydride, followed by an acid treatment and an alkali treatment to yield a compound of the formula:

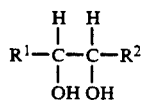
(IX)

wherein $R^1$ and $R^2$ are as defined above, reacting the compound of the formula (IX) with an acid to yield a compound of the formula:

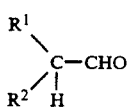
(VI)

wherein $R^1$ and $R^2$ are as defined above, and reacting the compound of the formula (VI) with a compound of the formula:

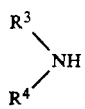
(VII)

wherein $R^3$ and $R^4$ are as defined above, in a solvent in the presence of a sulfonic acid.

The reaction of the compound of the formula (VI) with the compound of the formula (VII) is explained above PROCESS A.

The compound of the formula (VI) can be obtained by reacting the compound of the formula (IX) with an acid. This reaction is known as the pinacol-pinacoline rearrangement reaction. As the acid, there can be used acetic acid, propionic acid, phosphoric acid, sulfuric acid, etc. The reaction is carried out by charging the compound of the formula (IX) in an acid with stirring. The reaction temperature is preferably 60° to 130° C. The reaction time is preferably 30 minutes to 5 hours. The compound of the formula (VI) is obtained by pouring the reaction mixture into a large amount of ice water, filtering deposited crystals, drying and recrystallizing from isopropyl ether or the like.

The compound of the formula (IX) can be obtained by reducing the compound of the formula (VIII) with a metal hydride, followed by the acid treatment and the alkali treatment. As the metal hydride, there can be used LiAlH$_4$, NaBrH$_4$, etc. As the acid, there can be used hydrochloric acid, hydrobromic acid, hydroiodic acid, etc. As the alkali, there can be used sodium hydroxide, potassium hydroxide, sodium carbonate, potassium carbonate, etc. The reduction reaction is preferably carried out in a solvent such as anhydrous ethanol, or the like at 30° to 100° C. for 30 minutes to 5 hours. The compound of the formula (IX) can be obtained by pouring the reaction mixture into a large amount of ice water, filtering deposited crystals and recrystallizing from ethanol, or the like.

PROCESS C

The compound of the formula:

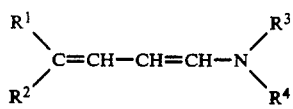
(I-2)

wherein $R^1$, $R^2$, $R^3$ and $R^4$ are as defined above, can be produced by reacting a compound of the formula:

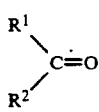
(III)

wherein $R^1$ and $R^2$ are as defined above, with a compound of the formula:

$$Ph_3P^+ {}^-ICH_3 \qquad (IV\text{-}2)$$

wherein Ph is a phenyl group, in a solvent in the presence of an alkoxide or an organometallic compound to yield a compound of the formula:

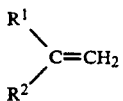

(X)

wherein R¹ and R² are as defined above, formylating the compound of the formula (X) in dimethylformamide in the presence of POCl₃ to yield a compound of the formula:

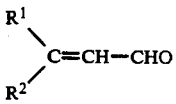

(XI)

wherein R¹ and R² are as defined above, reacting the compound of the formula (XI) with a compound of the formula:

$$Ph_3P^{+-}ClCH_2OCH_3 \quad \text{(IV-1)}$$

wherein Ph is a phenyl group, in a solvent in the presence of an alkoxide or an organometallic compound to yield a compound of the formula:

(XII)

wherein R¹ and R² are as defined above, hydrolyzing the compound of the formula (XII) with an acid, followed by an alkali treatment to yield a compound of the formula:

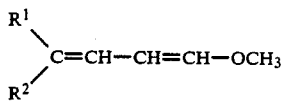

(XIII)

wherein R¹ and R² are as defined above, and reacting the compound of the formula (XIII) with a compound of the formula:

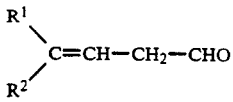

(VII)

wherein R³ and R⁴ are as defined above, in a solvent in the presence of a sulfonic acid.

The reaction of the compound of the formula (XIII) with the compound of the formula (VII) in a solvent in the presence of a sulfonic acid to yield the desired enamine derivative of the formula (I-2) can be carried out in the same manner as mentioned in the reaction of the compound of the formula (VI) with the compound of the formula (VII) in PROCESS A.

The compound of the formula (XIII) can be obtained by hydrolyzing the compound of the formula (XII) with an acid, and if required, followed by an alkali treatment, in the same manner as described in the hydrolysis of the compound of the formula (V), and if required, followed by the alkali treatment to yield the compound of the formula (VI) in PROCESS A.

The compound of the formula (XII) can be obtained by reacting the compound of the formula (XI) with the compound of the formula (IV-1) in a solvent in the presence of an alkoxide or an organometallic compound, in the same manner as described in the reaction of the compound of the formula (III) with the compound of the formula (IV-1) in a solvent in the presence of an alkoxide or an organometallic compound, that is, the Wittig reaction, in PROCESS A.

The compound of the formula (XI) can be obtained by formylating the compound of the formula (X) in dimethylformamide in the presence of POCl₃. This reaction is generally known as the Vilsmeier reaction. The reaction temperature is preferably 0° to 80° C. The reaction time is preferably 30 minutes to 5 hours.

The compound of the formula (X) can be obtained by reacting the compound of the formula (III) with the compound of the formula (IV-2) in a solvent in the presence of an alkoxide, or an organometallic compound in the same manner as described in the reaction of the compound of the formula (III) with the compound of the formula (IV) in a solvent in the presence of an alkoxide or an organometallic compound, that is, the Wittig reaction, in PROCESS A.

PROCESS D

The enamine derivative of the formula:

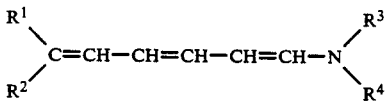

(I-3)

wherein R¹, R², R³ and R⁴ are as defined above, can be produced by reacting a compound of the formula:

(III)

wherein R¹ and R² are as defined above, with a compound of the formula:

$$Ph_3P^{+-}ICH_3 \quad \text{(IV-2)}$$

wherein Ph is a phenyl group, in a solvent in the presence of an alkoxide or an organometallic compound to yield a compound of the formula:

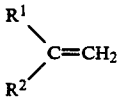

(X)

wherein R¹ and R² are as defined above, formylating the compound of the formula (X) in dimethylformamide in the presence of POCl₃ to yield a compound of the formula:

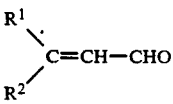

(XI)

wherein R¹ and R² are as defined above, reacting the compound of the formula (XI) with the compound of the formula (IV-2) in a solvent in the presence of an alkoxide or an organometallic compound to yield a compound of the formula:

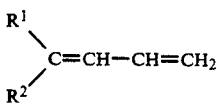
(XIV)

wherein $R^1$ and $R^2$ are as defined above, formylating the compound of the formula (XIV) in dimethylformamide in the presence of $POCl_3$ to yield a compound of the formula:

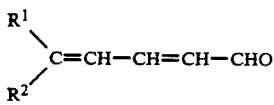
(XV)

wherein $R^1$ and $R^2$ are as defined above, reacting the compound of the formula (XV) with a compound of the formula:

(IV-1)

wherein Ph is a phenyl group, in a solvent in the presence of an alkoxide or an organometallic compound to yield a compound of the formula:

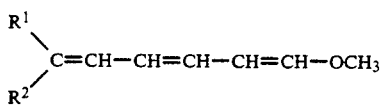
(XVI)

wherein $R^1$ and $R^2$ are as defined above, hydrolyzing the compound of the formula (XVI) with an acid, followed by an alkali treatment to yield a compound of the formula:

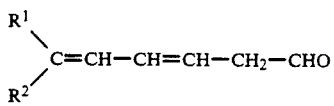
(XVII)

wherein $R^1$ and $R^2$ are as defined above, and reacting the compound of the formula (XVII) with a compound of the formula:

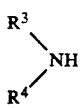
(VII)

wherein $R^3$ and $R^4$ are as defined above, in a solvent in the presence of a sulfonic acid.

The enamine derivative of the formula (I-3) can be produced by reacting the compound of the formula (XVII) with the compound of the formula (VII) in a solvent in the presence of a sulfonic acid in the same manner as described in the reaction of the compound of the formula (VI) with the compound of the formula (VII) in PROCESS A.

The compound of the formula (XVII) can be produced by hydrolyzing the compound of the formula (XVI) with an acid, and if required, followed by an alkali treatment in the same manner as described in the hydrolysis of the compound of the formula (V) with an acid, and if required, followed by an alkali treatment to yield the compound of the formula (VI) in PROCESS A.

The compound of the formula (XVI) can be obtained by reacting the compound of the formula (XV) with the compound of the formula (IV-1) in a solvent in the presence of an alkoxide or an organometallic compound in the same manner as described in the reaction of the compound of the formula (III) with the compound of the formula (IV) in a solvent in the presence of an alkoxide or an organometallic compound, that is, the Wittig reaction, in PROCESS A.

The compound of the formula (XV) can be obtained by formylating the compound of the formula (XIV) in dimethylformamide in the presence of $POCl_3$. This reaction is known as the Vilsmeier reaction. The reaction is preferably carried out at 0° to 80° C. for 30 minutes to 5 hours.

The compound of the formula (XIV) can be obtained by reacting the compound of the formula (XI) with the compound of the formula (IV-2) in a solvent in the presence of an alkoxide or an organometallic compound in the same manner as described in the reaction of the compound of the formula (III) with the compound of the formula (IV) in a solvent in the presence of an alkoxide or an organometallic compound, that is, the Wittig reaction in PROCESS A.

The compound of the formula (XI) can be obtained by formylating the compound of the formula (X) in dimethylformamide in the presence of $POCl_3$ This reaction is known as the Vilsmeier reaction. The reaction is preferably carried out at 0° to 80° C. for 30 minutes to 5 hours.

The compound of the formula (X) can be obtained by reacting the compound of the formula (III) with the compound of the formula (IV-2) in a solvent in the presence of an alkoxide or an organometallic compound in the same manner as described in the reaction of the compound of the formula (III) with the compound of the formula (IV) in a solvent in the presence of an alkoxide or an organometallic compound, that is, the Wittig reaction, in PROCESS A.

The enamine derivatives of the formula (I) are effective as a charge transport material in an electrophotographic plate.

The electrophotographic plate can be obtained by composing a photosensitive layer on an electroconductive substrate.

As the electroconductive substrate, there can be used paper or a plastic film subjected to electroconductive treatment, a plastic film laminated with a foil of metal such as aluminum, aluminum or the like electroconductive metal plate or drum, etc.

The photosensitive layer can be divided into two groups, one of which is a two layers type photoconductive layer comprising a charge generating layer and a charge transport layer wherein functions for generating charge and transporting charge are separated, and the other of which is one layer type photoconductive layer.

The two layers type photoconductive layer is explained below.

The charge generating layer includes an organic pigment which generates charge. As the organic pigment, there can be used azoxybenzenes, disazos, trisazos, benzimidazoles, polycyclic quinolines, indigoids, quinacridones, phthalocyanines, perylenes, methines, etc. These pigments are disclosed, for example, in U.S. Pat.

Nos. 3,898,084; 3,887,366; and 4,028,102; British Patent Nos. 1,370,197; 1,337,222; 1,337,224 and 1,402,967; Canadian Patent No. 1,007,095; and German Offenlegungsschrift 2,260,540. Particularly, $\tau$-, $\tau'$-, $\eta$- and $\eta'$-form metal-free phthalocyanines disclosed in U.S. Pat. No. 4,619,879 and European Patent Publication No. 92255 have high sensitivity even to a long wavelength and are effective as an electrophotographic plate for printer mounting a diode laser. It is also possible to use other organic pigments generating charge carriers by exposure to light.

The charge generating layer includes a binder and/or additives such as a plasticizer, a fluidity-imparting agent, and, if necessary, a pin hole controlling agent, etc.

As the binder, there can be used silicone resins, polyamide resins, polyurethane resins, polymethyl methacrylate resins, polyacrylamide resins, etc. Further, it is also possible to use heat and/or photo curable resins. Any resins which can form a coating having electrical insulating properties by a conventional process can be used. The binder is used in the charge generating layer in an amount of 300 parts by weight or less per 100 parts by weight of the organic pigment. When the amount is more than 300 parts by weight, there is a tendency to lower electrophotographic properties.

As the plasticizer, there can be used halogenated paraffins, dimethylnaphthalene, dibutyl phthalate, etc.

As the fluidity imparting agent, there can be used Modaflow (mfd. by Monsanto Chemical Co.), etc.

As the pin hole controlling agent, there can be used benzoin, dimethyl phthalate, etc.

These additives can be used in amounts of 5% by weight or less, respectively, based on the weight of the organic pigment.

The charge transport layer includes a charge transport material. As the charge transport material, there can be used the enamine derivative of the formula (I). It is possible to co-use other charge transport materials.

Examples of the other charge transport materials are 3-phenylcarbazole, 2-phenylindole, oxadiazole, oxatriazole, 1-phenyl-3-(4-diethylaminostyryl)-5-(4-diethylaminophenyl) pyrazoline, 2-phenyl-4-(4-diethylaminophenyl) -5-phenyloxazole, 2-(p-dimethylaminophenyl)-4-(p-dimethylamino) phenyl-5-(o-chlorophenyl)-1,3-oxazole, triphenylamine, imidazole, 2,7-dinitro-9-fluorenone, 2,4,7-trinitro-9-flurenone, 4H-indeno(1,2,6)thiophen-4-one, 1-bromopyrene, 2-phenylpyrene, poly-N-vinylcarbazole, polyvinylpyrene, polyvinylbenzothiophene, polyvinyl anthrathene, polyvinyl pyrazoline, etc. and derivatives thereof.

It is preferable to use the enamine derivative of the formula (I) in an amount of 10 to 100% by weight based on the total weight of the charge transport materials. When the amount of the enamine derivative of the formula (I) is too small, the photoresponse and durability are easily lowered. It is particularly preferable to use the enamine derivative of the formula (I) in an amount of 40 to 100% by weight based on the total weight of the charge transport materials.

The charge transport layer can also include a binder, additives such as a plastizer, a fluidity imprating agent, a pin hole controlling agent like the charge generating layer. The binder is preferably used in an amount of 400 parts by weight or less per 100 parts by weight of the charge transport materials so as not to lower electrophotographic properties. When only low-molecular weight charge transport materials such as the enamine derivative of the formula (I) are used, it is preferable to use the binder in an amount of 50% by weight or more considering film properties. The additives can preferably be used in an amount of 5% by weight or less based on the weight of the charge transport materials.

The two layers type photoconductive layer can be formed by laminating a charge generating layer and a charge transport layer in this order, or by laminating a charge transport layer and a charge generating layer in this order. It is also possible to take a sandwich structure wherein two charge generating layers sandwich a charge transport layer.

The thickness of the charge generating layer is preferably 0.001 to 10 $\mu$m, more preferably 0.2 to 5 $\mu$m. The thickness of the charge transport layer is preferably 5 to 50 $\mu$m, more preferably 8 to 20 $\mu$m. When the thickness of the charge generating layer is less than 0.001 $\mu$m, there is a tendency to lower the sensitivity, whereas when the thickness is more than 10 $\mu$m, there is a tendency to increase the residual potential. Further, when the thickness of the charge transport layer is less than 5 $\mu$m, there is a tendency to deteriorate the charging characteristics, whereas when the thickness is more than 50 $\mu$m, there is a tendency to lower the sensitivity.

The charge generating layer can be formed by a conventional vacuum deposition method in the case of using only the organic pigment mentioned above. It is also possible to form the charge generating layer by uniformly dissolving or dispersing an organic pigment, a binder and if necessary one or more additives in a solvent such as acetone, methyl ethyl ketone, tetrahydrofuran, toluene, xylene, methylene chloride, trichloroethane, or the like, coating the resulting solution or dispersion, and drying it.

Next, one layer type photoconductive layer is explained below.

The one layer type photoconductive layer includes a charge generating material and a charge transport material. As the charge generating material, there can be used the same organic pigments as used for the charge generating layer. As the charge transport material, there can be used the enamine derivative of the formula (I) alone or as a mixture with other charge transport material mentioned above. The amount of the enamine derivative of the formula (I) is 10 to 100% by weight based on the total weight of the charge transport materials.

The one layer type photoconductive layer may further contain a binder and one or more additives such as a plasticizer, a fluidity imparting agent, a pin hole controlling agent, etc., as in the case of the two layers type photoconductive layer. Among them, the role of the binder is important. The amount of the binder is preferably 80 to 450 parts by weight, more preferably 100 to 300 parts by weight, per 100 parts by weight of the charge transport material. If the amount of the binder is too small, the charging characteristics are deteriorated, whereas if the amount is too much, there is a tendency to lower the sensitivity. In this case, the charge generating material is used in an amount of preferably 0.1 to 20% by weight, more preferably 0.5 to 5% by weight based on the total weight of the charge transport material and the binder. If the amount of the charge generating material is too small, there is a tendency to lower the sensitivity, whereas if the amount is too much, there is a tendency to deteriorate the charging characteristics. The amounts of the additives such as the plasticizer, fluidity imparting agent, and pin hole controlling agent are 5% by weight or less in the one layer type photoconductive layer, respectively depending on purposes.

The thickness of the one layer type photoconductive layer is preferably 5 to 50 μm, more preferably 8 to 20 μm. If the thickness is less than 5 μm, there is a tendency to deteriorate the charging characteristics, whereas if the thickness is more than 50 μm, there is a tendency to lower the sensitivity.

The one layer type photoconductive layer can be formed by uniformly dissolving or dispersing a charge generating material, a charge transport material, a binder and other additives if necessary in a solvent in the same manner as described in the formation of the charge generating layer, coating it and drying it.

In this invention, it is also possible to employ as the photosensitive layer a multi layer type photoconductive layer wherein the same charge transport layer as used in the two layers type photoconductive layer is formed immediately on or under or both sides of the one layer type photoconductive layer.

The electrophotographic plate of this invention may further contain a thin adhesive layer or a barrier layer just on the electroconductive substrate and between the electroconductive substrate and the photosensitive layer. Further, a surface protective layer may be formed on the surface of electrophotographic plate.

This invention is illustrated by way of the following Examples, wherein all percents are by weight unless otherwise specified. Further, the following materials were used therein.

(1) Organic Pigment Generating Charge

Phthalocyanine: α-form metal-free phthalocyanine (H₂Pc) (mdf. by BASF AG).

(2) Charge Transport Materials (Comparison)
Pyrazoline derivative:
1-phenyl-3-(p-diethylaminostyryl)-5-(p-diethylaminophenyl) pyrazoline (PYZ)

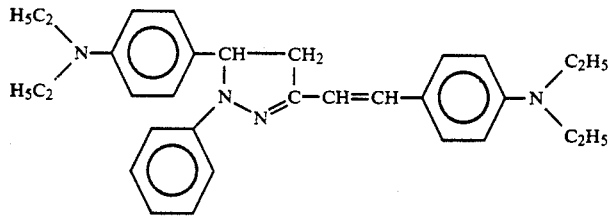

Oxazole derivative:
2-(p-dimetylamino)phenyl-4-(p-dimethylamino) phenyl-5-o-chlorophenyl-1,3-oxazole (OXZ)

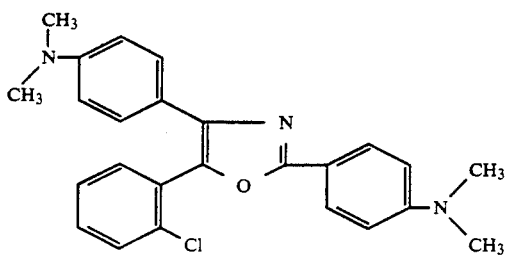

Hydrazone derivative: p-dimethylamino-(o-ethoxy) benzaldehydediphenylhydrazone (HYZ)

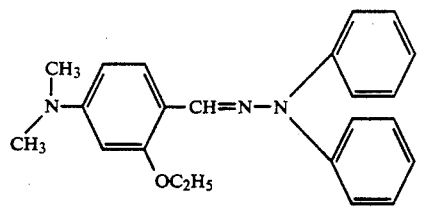

Enamine derivative: tetramethoxyphenylenamine (ENM)

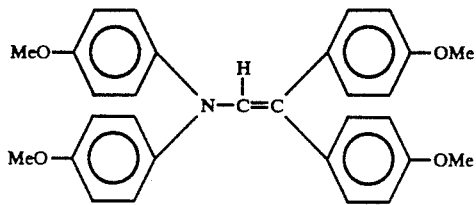

(3) Binder

Silicone varnish: KR-255 (solids content 50%) [mfd. by Sin-etsu Chemical Industry Co., Ltd.]

Polycarbonate resin: Iupilon S-2000 (solids content 50%) [mfd. by Mitsubishi Gas Chemical Co., Ltd.]

EXAMPLES 1 TO 24, COMPARATIVE EXAMPLES 1 TO 4

(a) In a ball mill (a pot having a diameter of about 10 cm, mfd. by Nippon Kagaku Kogyo Co., Ltd.), 2.5 g of H₂Pc, 5.0 g of silicone varnish and 92.5 g of methyl ethyl ketone were placed and kneaded for 8 hours. The resulting pigment dispersion was coated on an aluminum plate (an electroconductive layer) by using an applicator. After drying at 90° C. for 15 minutes, a charge generating layer having a thickness of 1 μm was formed. (b) A uniform coating composition for a charge transport layer comprising 10 g of a charge transport material as listed in Table 1, 10 g of Iupilon S-2000 as a binder, and 40 g of methylene chloride and 40 g of 1,1,2-trichloroethane as a solvent was prepared and immediately coated on the charge generating layer mentioned above so as to make the film thickness 15 μm after dried. After drying at 120° C. for 2 hours, a charge transport layer is formed to give an electrophotographic plate.

Electrophotographic plates obtained in Examples 1 to 24 and Comparative Examples 1 to 4 were subjected to measuring of electrophotographic properties, print resolution, photoresponse and durability as follows.

(i) Electrophotographic Properties

Using an electrophotographic plate cut to a size of 60 mm long and 70 mm wide, electrophotographic properties were measured by using an electrostatic recording paper analyzer (SP-428 mfd. by Kawaguchi Electric Works Co., Ltd.).

Initial potential $V_o$ in Table 1 means a charging potential obtained by fixing a sample on a revolving disc of SP-428, revolving at a rate of 1000 r.p.m. and subjecting to a corona discharge at about 5 KV for 10 seconds.

Dark decay $V_K$ means a potential decay after allowed to stand in the dark for 30 seconds after the corona discharge ($V_K = V_{30}/V_o \times 100$, $V_{30}$ means the potential after 30 seconds).

Half decay exposure $E_{50}$ means a light amount necessary for making the potential a half after exposing to a white light of 10 lux after measuring the dark decay.

Residual potential $V_R$ means a potential after exposure to the white light for 60 seconds.

(ii) Print Resolution

After the measurement of electrophotographic properties, the surface of electrophotographic plate was charged with corona discharge so as to make the surface potential $-600$ V to $-700$ V. Then, using as an original image an Electrophotographic Society Chart No. 1-T, exposure to a light image was conducted at 100 lus.s, followed by development with positively charged toner. The resulting toner image was transferred to a white sheet of paper, followed by fixation to give a test image. The print resolution was evaluated by the distinguishable number of fine lines per 1 mm. In each test, the same toner, and the same transfer and fixation methods were employed.

In Table 1, the electrophotographic properties and print resolution immediately after the production of electrophotographic plates (initial values) were measured and listed. Further, after repeating 10000 times of corona charging (surface potential $-1000$ V$\pm 100$ V) and removal of charging (exposure to light of a wavelength of 500 nm : a light amount 50 mJ/m$^2$) on each sample of electrophotographic plate (60 mm x 70 mm), the electrophotographic properties and print resolution were measured and listed in Table 1.

(iii) Photoresponse

The electrophotographic plates obtained in Examples 1 to 24 and Comparative Examples 1 to 4 were subjected to photoresponse test using a light decay measuring apparatus (Cincia 30, mfd. by Midoriya Denki K. K.). The surface potential of photosensitive layer was previously adjusted to $-700$ V by corona charging.

In the case of the samples of Examples 1 to 14 and Comparative Examples 1 to 4, the following method was employed.

A sample was then subjected to exposure to a light having a wavelength of 660 nm obtained by filtering a light from a halogen lamp with a diffraction grating for 50 msec, and then decay of surface potential of the photosensitive layer with the lapse of time was measured and plotted in graphs. The total exposure light energy was 20 mJ/m$^2$.

Figure 2:
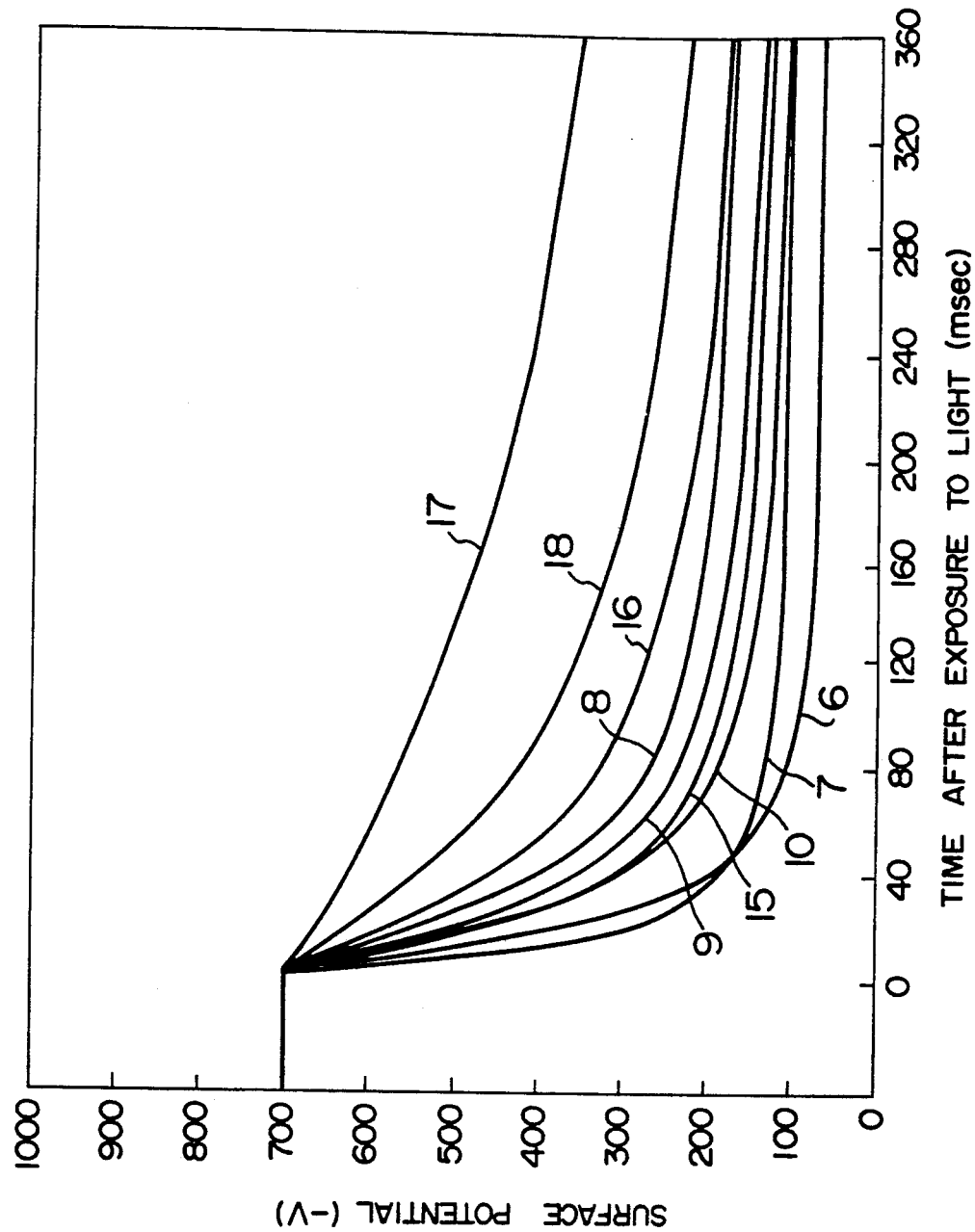
Figure 3:
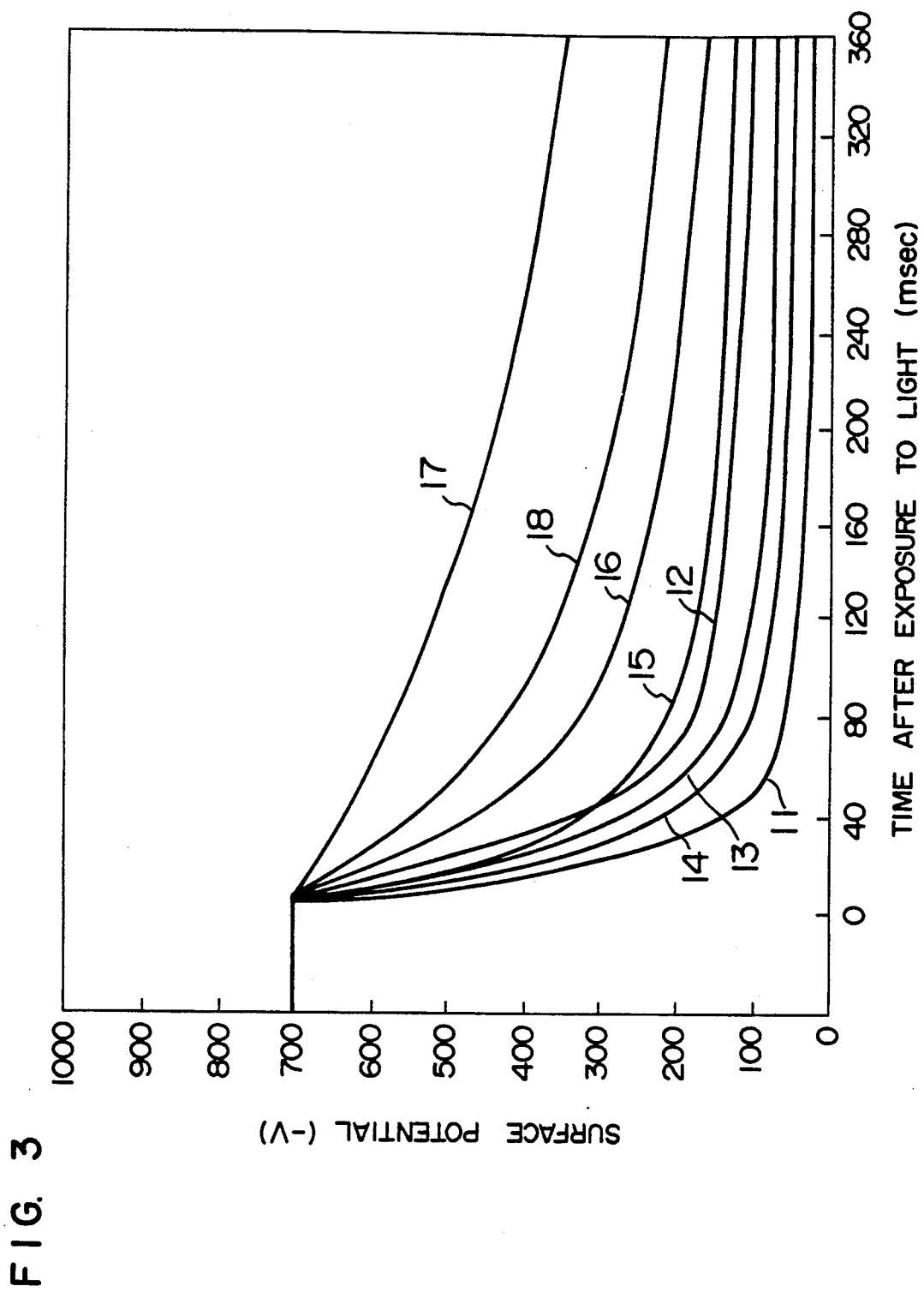

The results are shown in FIGS. 1 to 3. In FIG. 1, the curves 1 to 5 correspond to Examples 1 to 5. In FIG. 2, the curves 6 to 10 correspond to Examples 6 to 10. In FIGS. 1 and 2, the curves 15 to 18 correspond to Comparative Examples 1 to 4. In FIG. 3, the curves 11 to 14 correspond to Examples 11 to 14.

In the case of the samples of Examples 15 to 24 and Comparative Examples 1 to 4, the following method was employed.

A sample was then subjected to exposure to a light having a wavelength of 600 nm obtained from light emission diode (LED) for 1 msec, and then a time (t ½) necessary for decaying the surface potential of the photosensitive layer to a half ($-350$ V) of the initial value was measured. The total exposure light energy was 50 mJ/m$^2$.

The results are shown in Table 2.

TABLE 1

| Example No. | Charge transport material Kind of compound | Compound No. | Electrophotographic properties and print resolution (initial values) $V_o$ ($-$V) | $V_K$ (%) | $E_{50}$ (lux·s) | $V_R$ ($-$V) | Print resolution (no./mm) | Electrophotographic properties and print resolution (after treatment) $V_o$ ($-$V) | $V_K$ (%) | $E_{50}$ (lux·s) | $V_R$ ($-$V) | Print resolution (no./mm) |
|---|---|---|---|---|---|---|---|---|---|---|---|---|
| Example 1 | Enamine derivative | 1 | 1050 | 75 | 1.3 | 0 | 12.5 | 1060 | 75 | 1.3 | 0 | 12.5 |
| Example 2 | Enamine derivative | 2 | 1040 | 75 | 1.5 | 0 | 12.5 | 1050 | 75 | 1.4 | 0 | 12.5 |
| Example 3 | Enamine derivative | 3 | 1000 | 72 | 1.2 | 0 | 12.5 | 1040 | 73 | 1.2 | 0 | 10.0 |
| Example 4 | Enamine derivative | 4 | 1020 | 74 | 1.2 | 0 | 12.5 | 1000 | 74 | 1.2 | 0 | 10.0 |
| Example 5 | Enamine derivative | 5 | 1080 | 76 | 1.5 | 0 | 12.5 | 1080 | 76 | 1.5 | 0 | 10.0 |
| Example 6 | Enamine derivative | 6 | 1000 | 77 | 1.6 | 0 | 12.5 | 1110 | 77 | 1.5 | 0 | 10.0 |
| Example 7 | Enamine derivative | 7 | 1000 | 77 | 1.4 | 0 | 12.5 | 1120 | 78 | 1.4 | 0 | 12.5 |
| Example 8 | Enamine derivative | 8 | 1150 | 78 | 1.7 | 0 | 12.5 | 1150 | 78 | 1.7 | 0 | 12.5 |
| Example 9 | Enamine derivative | 9 | 1120 | 77 | 1.9 | 0 | 12.5 | 1120 | 78 | 1.8 | 0 | 12.5 |
| Example 10 | Enamine derivative | 10 | 1100 | 80 | 1.7 | 0 | 12.5 | 1220 | 81 | 1.7 | 0 | 12.5 |
| Example 11 | Enamine derivative | 11 | 950 | 70 | 0.8 | 0 | 12.5 | 980 | 70 | 0.8 | 0 | 10.0 |
| Example 12 | Enamine derivative | 12 | 1020 | 75 | 1.5 | 0 | 12.5 | 1030 | 76 | 1.5 | 0 | 12.5 |
| Example 13 | Enamine derivative | 13 | 1040 | 75 | 1.4 | 0 | 12.5 | 1070 | 76 | 1.4 | 0 | 12.5 |

TABLE 1-continued

| Example No. | Charge transport material Kind of compound | Compound No. | Electrophotographic properties and print resolution (initial values) | | | | | Electrophotographic properties and print resolution (after treatment) | | | | |
|---|---|---|---|---|---|---|---|---|---|---|---|---|
| | | | $V_o$ (−V) | $V_K$ (%) | $E_{50}$ (lux·s) | $V_R$ (−V) | Print resolution (no./mm) | $V_o$ (−V) | $V_K$ (%) | $E_{50}$ (lux·s) | $V_R$ (−V) | Print resolution (no./mm) |
| Example 14 | Enamine derivative | 14 | 1010 | 76 | 1.2 | 0 | 12.5 | 1010 | 76 | 1.2 | 0 | 12.5 |
| Example 15 | Enamine derivative | 15 | 1030 | 75 | 1.2 | 0 | 12.5 | 1040 | 75 | 1.4 | 0 | 12.5 |
| Example 16 | Enamine derivative | 20 | 1070 | 80 | 1.6 | 0 | 12.5 | 1050 | 76 | 1.5 | 0 | 12.5 |
| Example 17 | Enamine derivative | 24 | 1010 | 72 | 1.1 | 0 | 12.5 | 1090 | 71 | 1.2 | 0 | 10.0 |
| Example 18 | Enamine derivative | 28 | 1000 | 76 | 1.5 | 0 | 12.5 | 1090 | 79 | 1.3 | 0 | 12.5 |
| Example 19 | Enamine derivative | 30 | 1080 | 73 | 1.3 | 0 | 12.5 | 1180 | 77 | 1.2 | 0 | 10.0 |
| Example 20 | Enamine derivative | 35 | 1020 | 78 | 1.2 | 0 | 12.5 | 1150 | 72 | 1.5 | 0 | 10.0 |
| Example 21 | Enamine derivative | 42 | 1140 | 72 | 1.4 | 0 | 12.5 | 1120 | 74 | 1.5 | 0 | 12.5 |
| Example 22 | Enamine derivative | 51 | 1060 | 77 | 1.4 | 0 | 12.5 | 1090 | 74 | 1.6 | 0 | 12.5 |
| Example 23 | Enamine derivative | 58 | 1090 | 73 | 1.3 | 0 | 12.5 | 1140 | 76 | 1.8 | 0 | 10.0 |
| Example 24 | Enamine derivative | 61 | 1050 | 74 | 1.6 | 0 | 12.5 | 1080 | 78 | 1.8 | 0 | 10.0 |
| Comparative Example 1 | Pyrazoline derivative | PYZ | 880 | 60 | 1.8 | 0 | 12.5 | 720 | 52 | 1.6 | 0 | 1.6 |
| Comparative Example 2 | Oxazole derivative | OXZ | 900 | 62 | 2.0 | 0 | 12.5 | 860 | 58 | 1.9 | 0 | 3.2 |
| Comparative Example 3 | Hydrazone derivative | HYZ | 1100 | 75 | 2.4 | 0 | 12.5 | 1150 | 76 | 2.6 | 50 | 8.0 |
| Comparative Example 4 | Enamine derivative | ENM | 1040 | 74 | 2.2 | 0 | 12.5 | 1100 | 75 | 2.3 | 20 | 10.0 |

TABLE 2

| Example No. | Charge transport material Kind of compound | Compound No. | Photo-response $t\frac{1}{2}$ (msec) |
|---|---|---|---|
| Example 15 | Enamine derivative | 15 | 7 |
| Example 16 | Enamine derivative | 20 | 18 |
| Example 17 | Enamine derivative | 24 | 9 |
| Example 18 | Enamine derivative | 28 | 25 |
| Example 19 | Enamine derivative | 30 | 21 |
| Example 20 | Enamine derivative | 35 | 13 |
| Example 21 | Enamine derivative | 42 | 19 |
| Example 22 | Enamine derivative | 51 | 18 |
| Example 23 | Enamine derivative | 58 | 10 |
| Example 24 | Enamine derivative | 61 | 20 |
| Comparative Example 1 | Pyrazoline derivative | PYZ | 42 |
| Comparative Example 2 | Oxazole derivative | OXZ | 55 |
| Comparative Example 3 | Hydrazone derivative | HYZ | 93 |
| Comparative Example 4 | Enamine derivative | ENM | 68 |

As is clear from the results shown in Table 1, the electrophotographic plates obtained in Examples 1 to 24 have $V_o$ of 1000 V or more in the absolute values and thus are excellent in charging characteristics, have $E_{50}$ of less than 2.0 lux.s and are excellent in the sensitivity and small in the dark decay. Further, even after repeating the corona charging and removal of charging 10,000 times, the electrophotographic properties are not lowered and the print resolution was 10.0 to 12.5 number/mm, which values are almost the same as those of initial values: this means that durability is also excellent.

In contrast, the electrophotographic plates obtained in Comparative Examples 1 and 2 are low in $V_o$ and $V_K$, deteriorated in charging properties, and large in the dark decay. Further, after repeating 10000 times of corona charging and removal of charging, not only these properties are lowered but also the print resolution is remarkably lowered to deteriorate the durability. The electrophotographic plates obtained in Comparative Examples 3 and 4 are inferior in the sensitivity, and the residual potential is increased after repeating 10000 times of the corona charging and removal of charging. In addition, the electrophotographic plate obtained in Comparative Example 3 is considerably lowered in the resolving power and inferior in the durability.

Further, as is clear from the results shown in FIGS. 1 to 3 and Table 2, the electrophotographic plates obtained in Examples 1 to 24 are remarkably superior to those obtained in Comparative Examples 2 to 4 in the photoresponse. The electrophotographic plate obtained in Comparative Example 1 shows almost the same photoresponse as those obtained in Examples 1 to 24, but is inferior in the charging characteristics, large in the dark decay and inferior in the durability.

As mentioned above, the electrophotographic plate obtained in Examples 1 to 24 are excellent in the sensitivity, photoresponse and durability.

The enamine derivatives (Compound Nos. 11 to 14) used in Examples 11 to 14 were synthesized as follows.

SYNTHESIS EXAMPLE

[Synthesis of
1,1-bis(p-diethylaminophenyl)-methoxyethylene
(Compound (a))]

To 105 ml of dry tetrahydrofuran (THF) containing 15 g of methoxymethyltriphenylphosphonium chloride, 27 ml of n-butyllithium (n-hexane solution 1.6 mole/l) was added dropwise gradually in a nitrogen stream at 5° C. with stirring. After dissolving the starting material, the stirring was continued at that temperature for 2.5 hours. After adding 140 ml of THF containing 14 g of 4'-bisdiethylaminobenzophenone dropwise, the reaction was carried out at room temperature for 3 hours. Then, the reaction mixture was poured into 500 ml of water, followed by extraction with benzene. After dried, the benzene was removed by distillation. The residue was purified with a silica gel column to yield 8.1 g of compound (a) in 53% yield.

Figure 4:
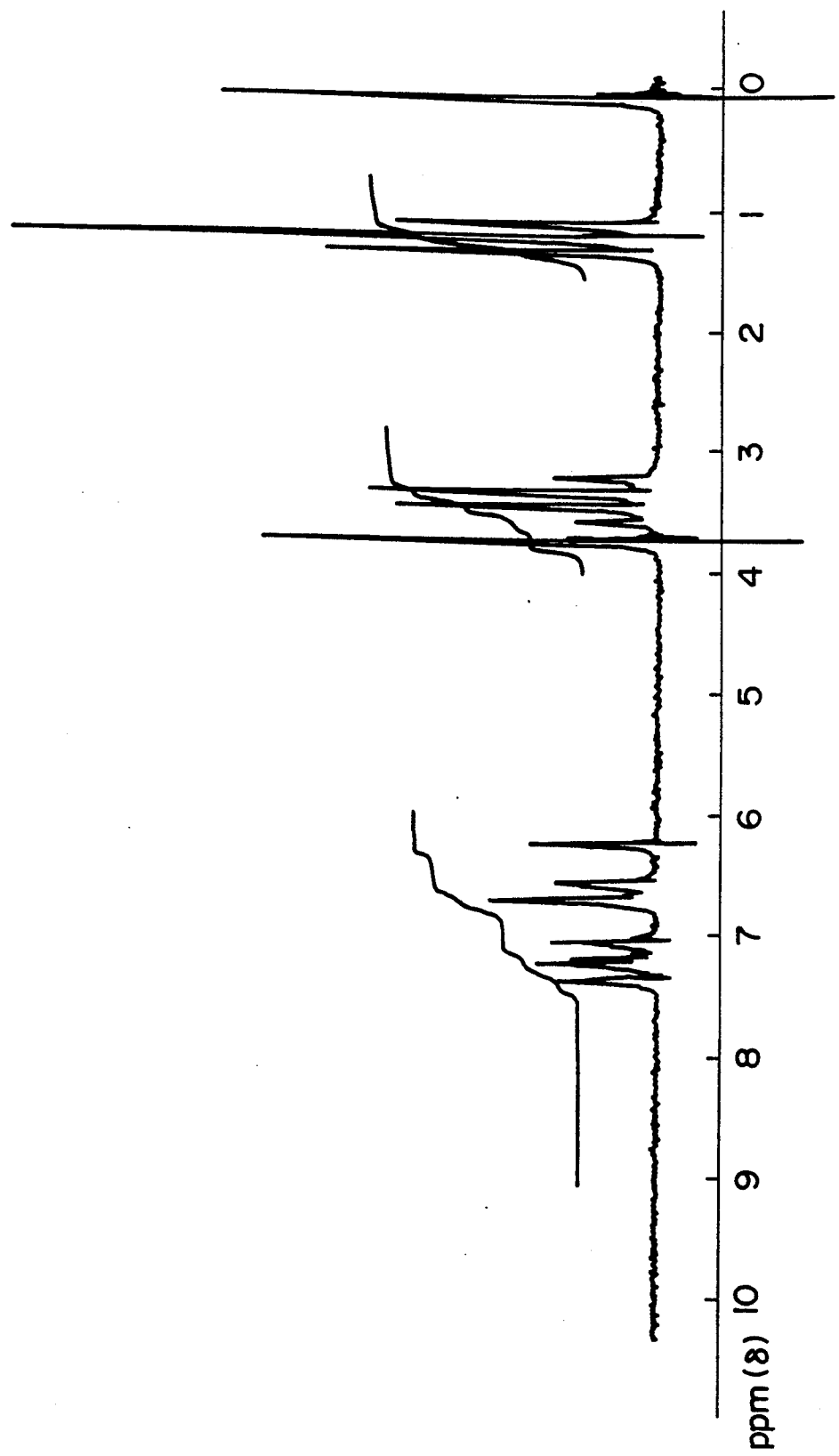
FIGS. 4, 5, 7, 8, 10, 12, 13, 14 and 15 are NMR spectra of enamine derivatives obtained in Examples of this invention.

NMR (CDCl$_3$): δ=1.1 (t 12H —CH$_2$—CH$_3$); 3.3 (q 8H —CH$_2$—CH$_3$); 3.6 (s 3H C=CH—OCH$_3$); 6.1 (s 1H C=CH—OCH$_3$); 6.4-7.2 (m 8H arom.). Melting point (oily matter):

NMR spectrum of Compound (a) is shown in FIG. 4.

SYNTHESIS EXAMPLE 2

[Synthesis of
1,1-bis(p-diethylaminophenyl)acetaldehyde
(Compound (b))]

Compound (a) in an amount of 7.5 g was dissolved in 60 ml of 60% perchloric acid aqueous solution at 20° C. or lower and stirred for 20 minutes. Then the solution was made alkaline with a sodium hydroxide aqueous solution under cooling. The deposited sirupy material was extracted with benzene, followed by drying. After removal of the benzene by distillation, the residue was recrystallized from methanol to give 4.8 g of compound (b) in yield of 67%.

NMR (CDCl$_3$): δ=1.1 (t 12H —CH$_2$—CH$_3$); 3.3 (q 8H —CH$_2$—CH$_3$); 4.6 (d 1H=CH—CHO); 9.7 (d 1H=CH—CHO); 6.5-7.0 (m 8H arom.).

IR (KBr): 1724 cm$^{-1}$ (—CHO)

Melting point: 74.5°-76.5° C.

Figure 5:
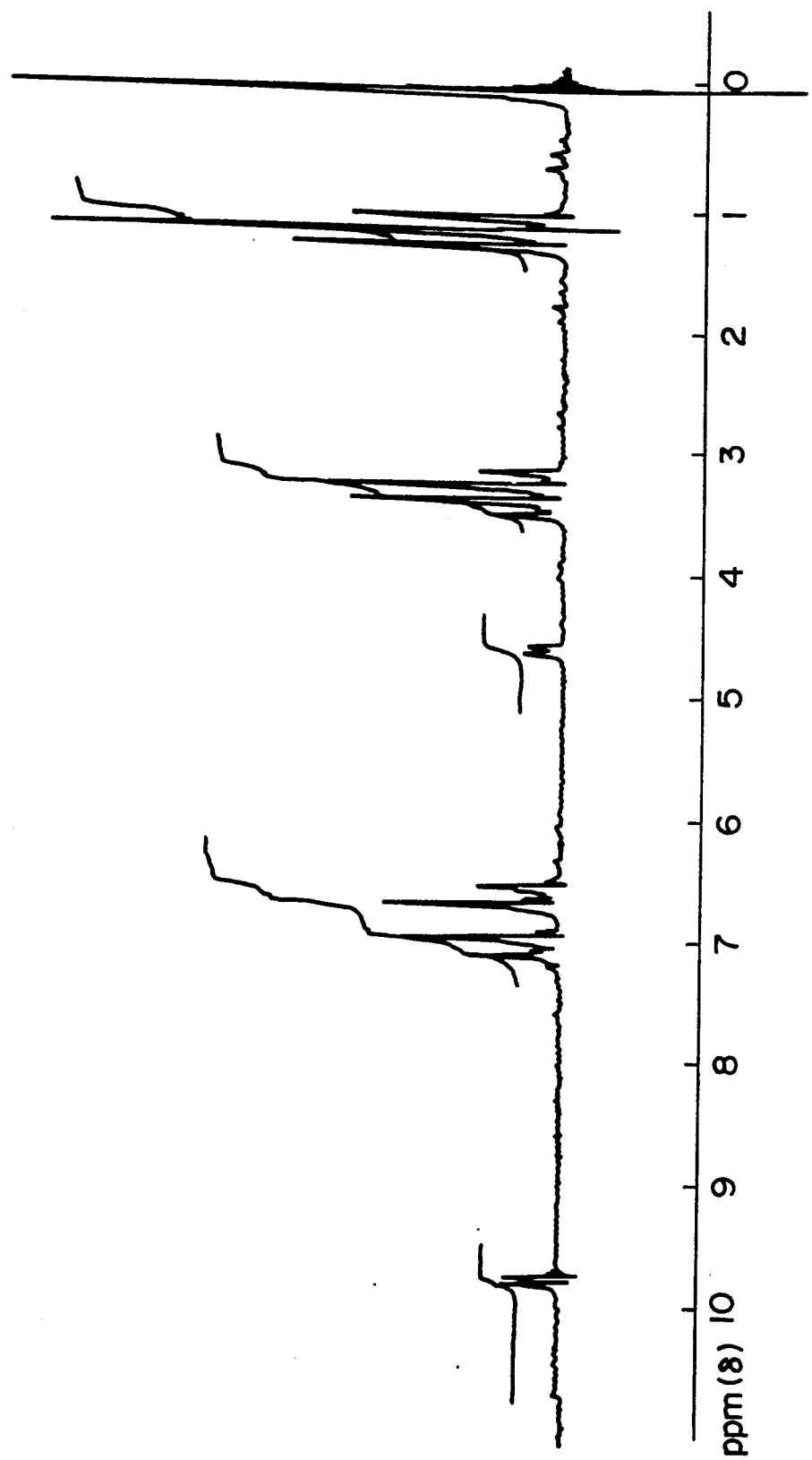
Figure 6:
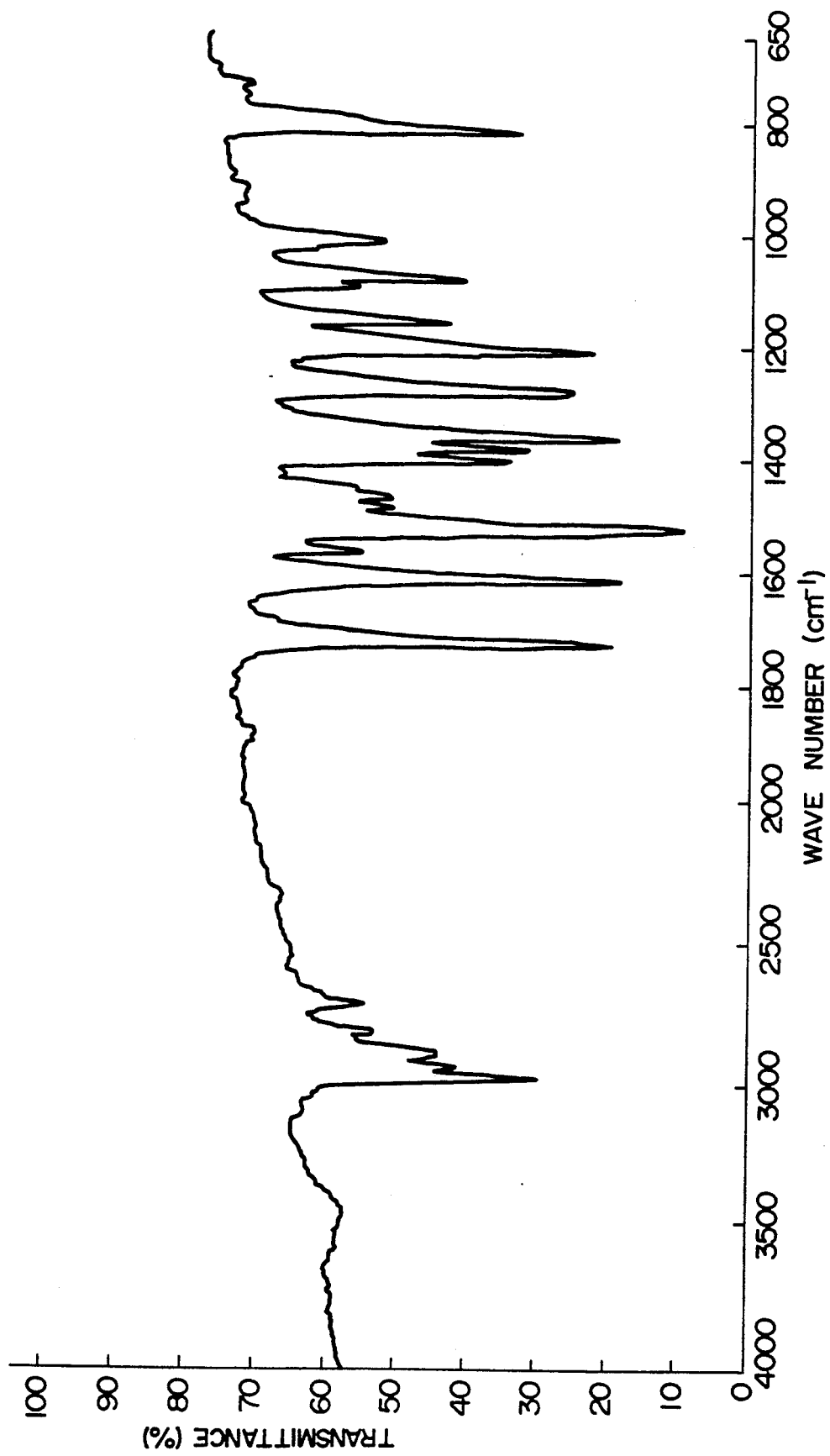
FIGS. 6, 9 and 11 are infrared spectra of enamine derivatives obtained in Examples of this invention.

NMR spectrum of Compound (b) is shown in FIG. 5, and IR spectrum of compound (b) is shown in FIG. 6.

SYNTHESIS EXAMPLE 3

[Synthesis of
1,1-bis(p-dimethylaminophenyl)-methoxyethylene
(Compound (c))]

Compound (c) was synthesized from 4,4'-bis(p-dimethylamino)benzophenone in the same manner as described in Synthesis Example 1 in 66% yield.

NMR (CDCl$_3$): δ=2.9 (s 12H —N—CH$_3$); 3.6 (s 3H C=CH—O—CH$_3$); 6.2 (s 1H C=CH—O—CH$_3$); 6.5-7.3 (m 8H arom.).

Melting point: 89.5°-91° C.

Figure 7:
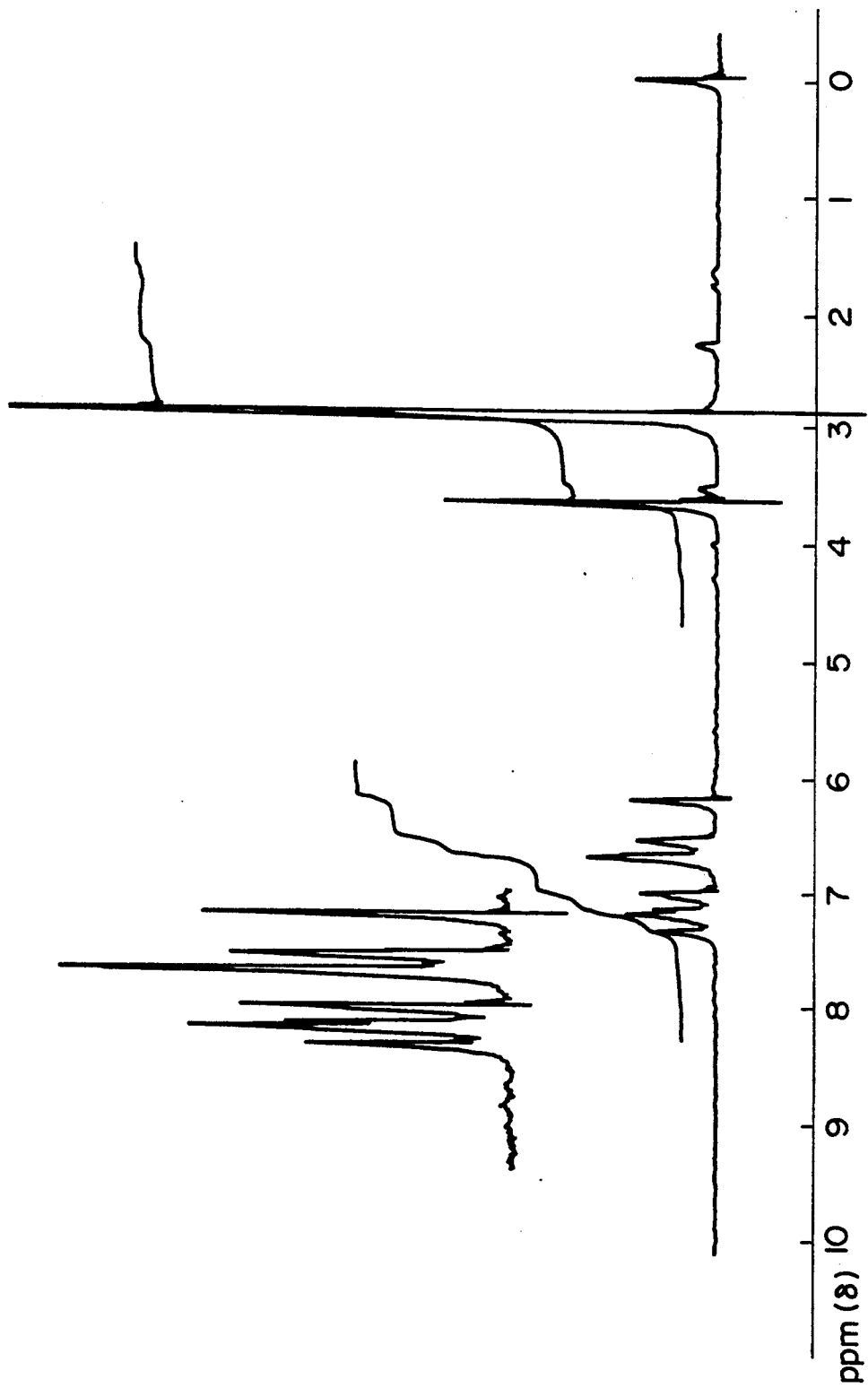

NMR spectrum of Compound (c) is shown in FIG. 7.

SYNTHESIS EXAMPLE 4

[Synthesis of
1,1-bis(p-dimethylaminophenyl)acetaldehyde
(Compound (d))]

Compound (d) was synthesized from Compound (c) in the same manner as described in Synthesis Example 2 in 62% yield.

NMR (CDCl$_3$): δ=2.9 (s 12H —N—CH$_3$); 4.7 (d 1H=CH—CHO); 9.8 (d 1H=CH—CHO); 6.6-7.6 (m 8H arom.).

IR (KBr): 1722 cm (—CHO).

Melting point: 72°-75° C.

Figure 8:
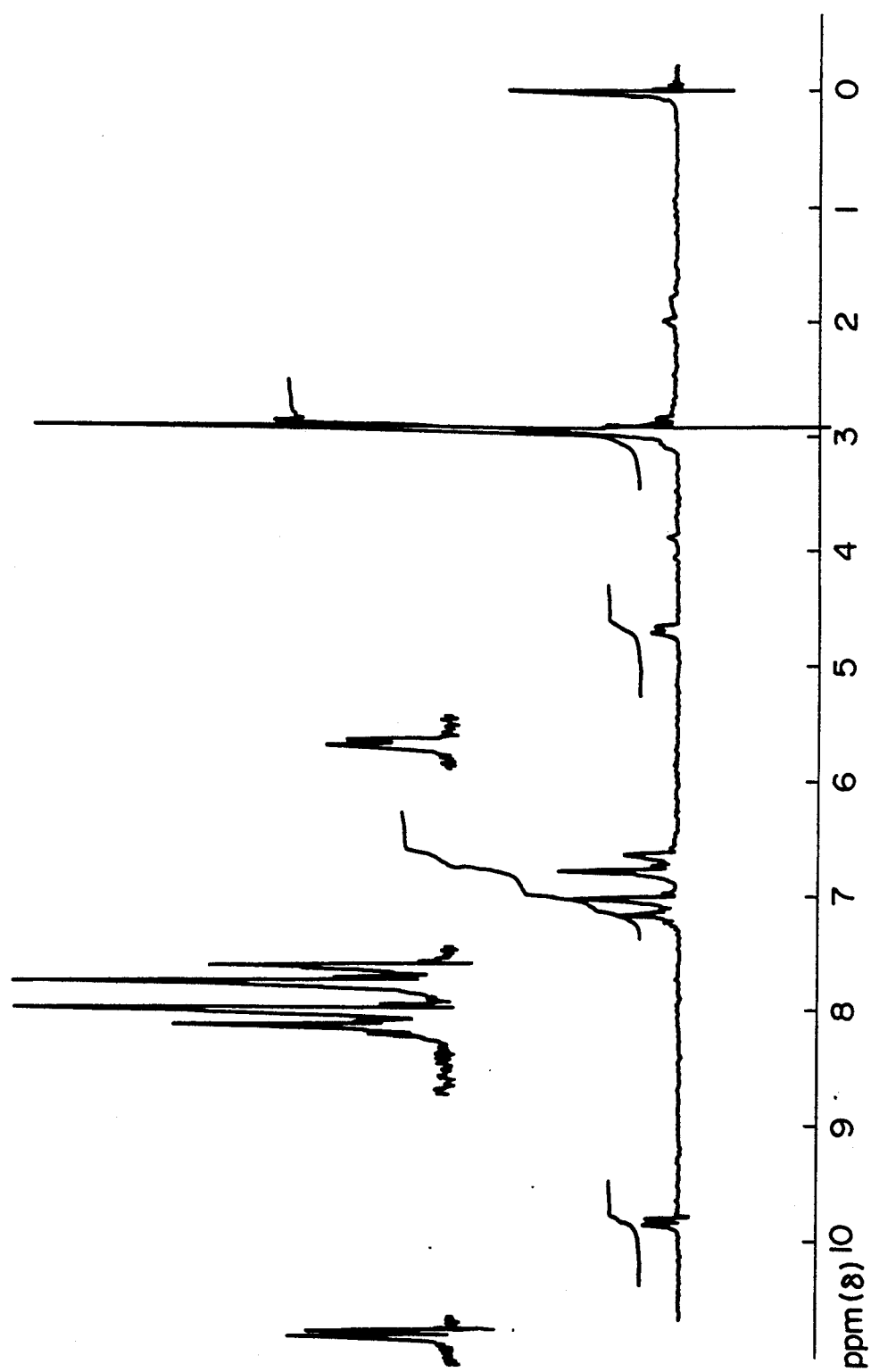
Figure 9:
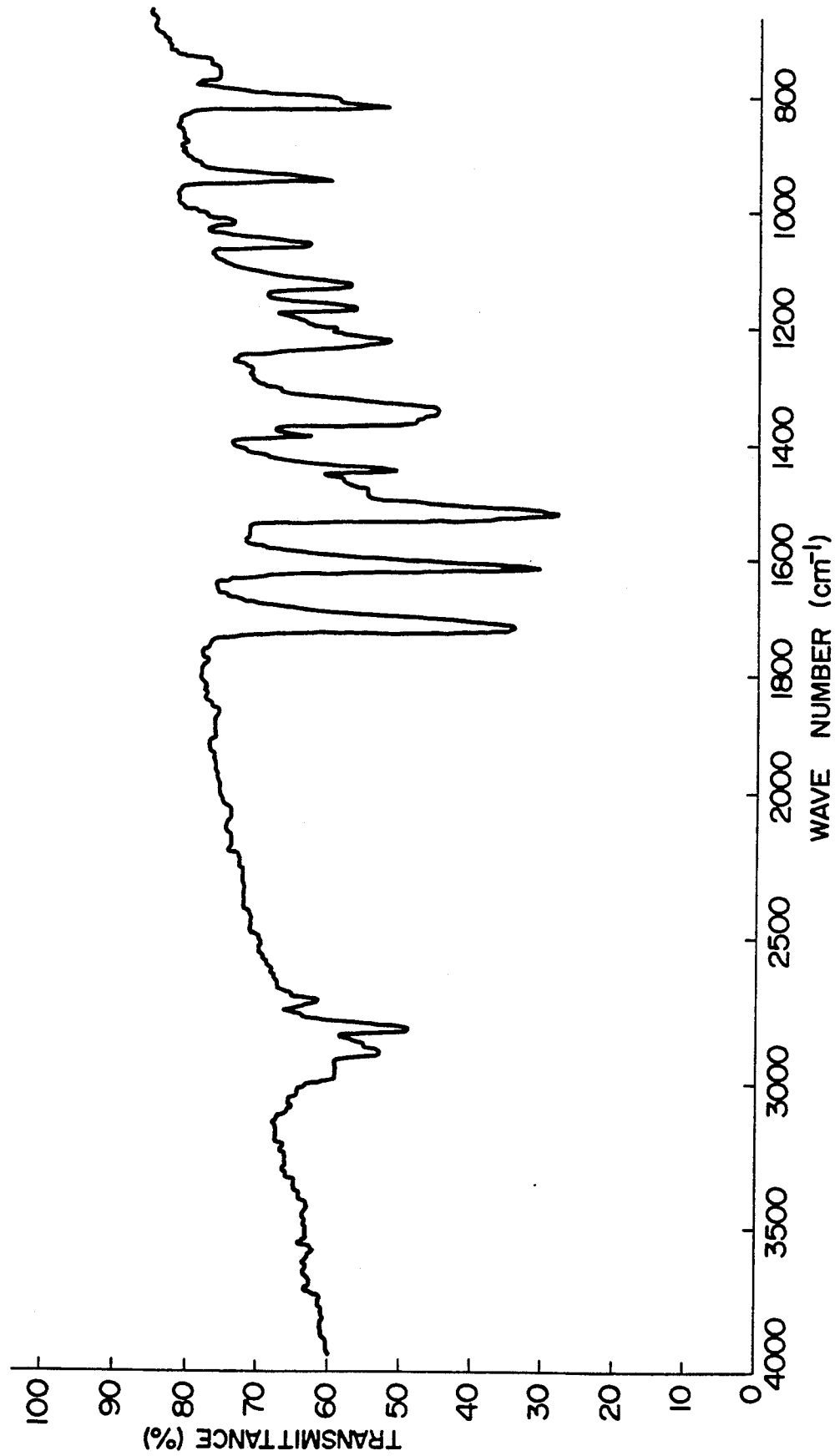

NMR spectrum of Compound (d) is shown in FIG. 8, and IR spectrum of Compound (d) is shown in FIG. 9.

SYNTHESIS EXAMPLE 5

[Synthesis of 1,1-bis(p-methoxyphenyl)acetaldehyde
(Compound (e))]

In 3 liters of dry ethanol, 75 g of 4,4'-bismethoxybenzoin and 21 g of sodium borohydride were refluxed for 2 hours. After adding 250 ml of concentrated hydrochloric acid to the reaction mixture, the resulting mixture was poured into 1300 ml of ice water, followed by filtration of deposited crystals. After recrystallized from 95% ethanol, there was obtained 57 g of 1,2-di(p-methoxyphenyl)ethane-1,2-diol, which was then added to 570 ml of 80% acetic acid and stirred at 90° C. for 50 minutes. Then, the reaction mixture was poured into 4 liters of ice water and deposited crystals were filtered. After drying, the crystals were recrystallized from isopropyl ether to give 40 g of Compound (e) in 69% yield.

NMR (CDCl$_3$): δ=3.8 (s 6H —OCH$_3$); 4.7 (d 1H=CH—CHO); 9.8 (d 1H=CH—CHO); 6.7-7.2 (m 8H arom.).

IR (KBr): 1722 cm$^{-1}$ (—CHO).

Melting point: 101°-103° C.

Figure 10:
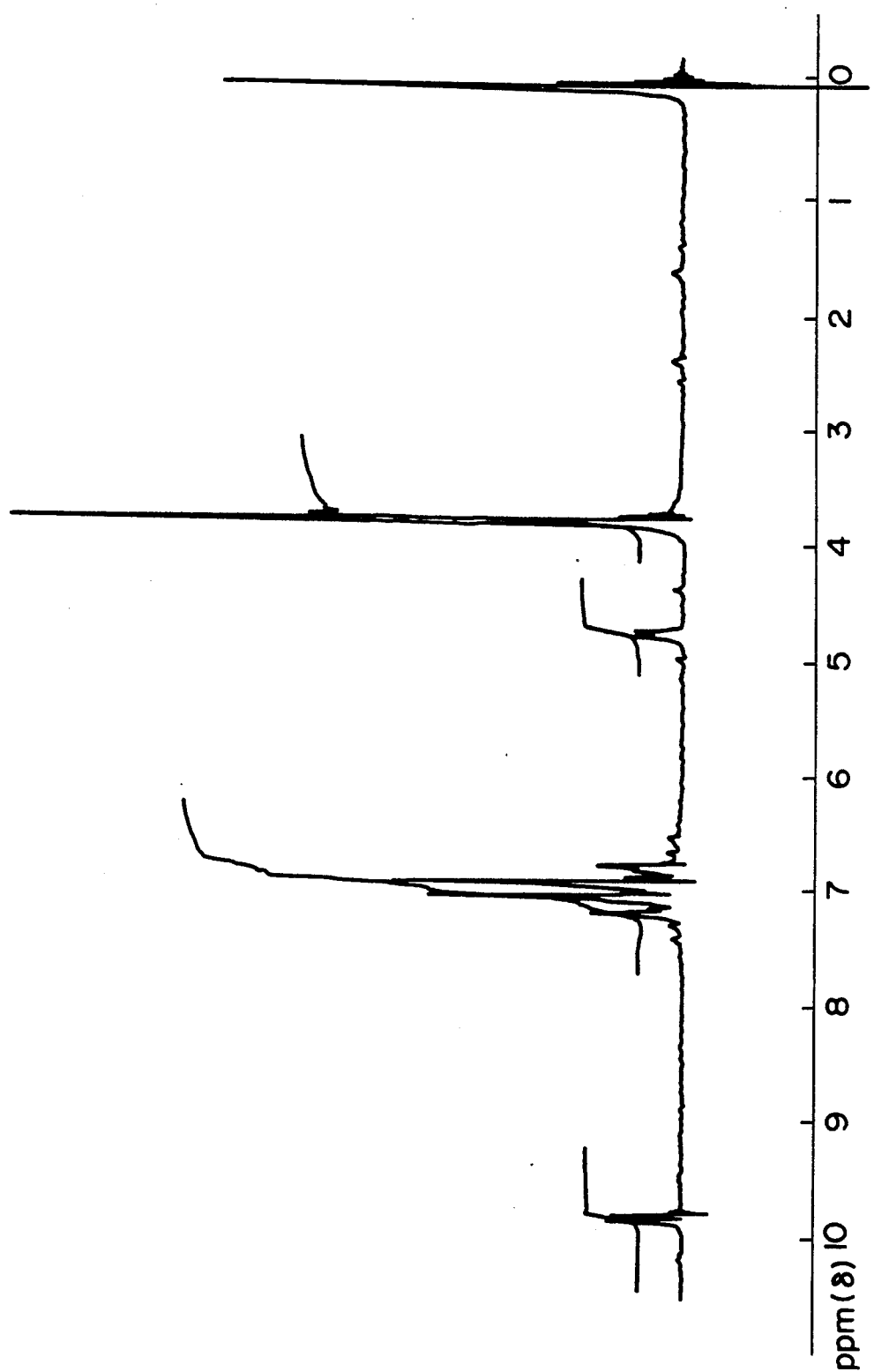
Figure 11:
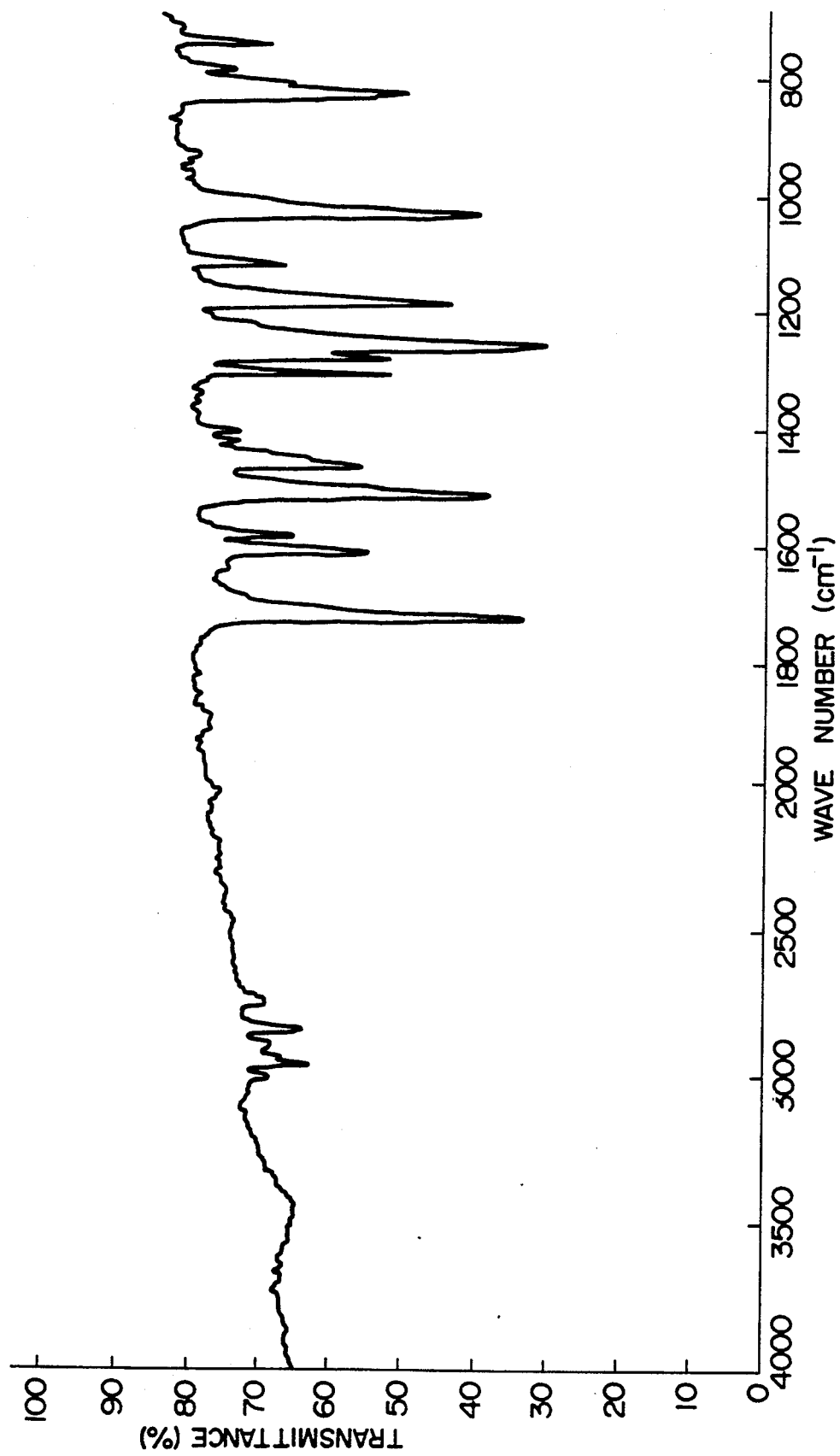
Figure 12:
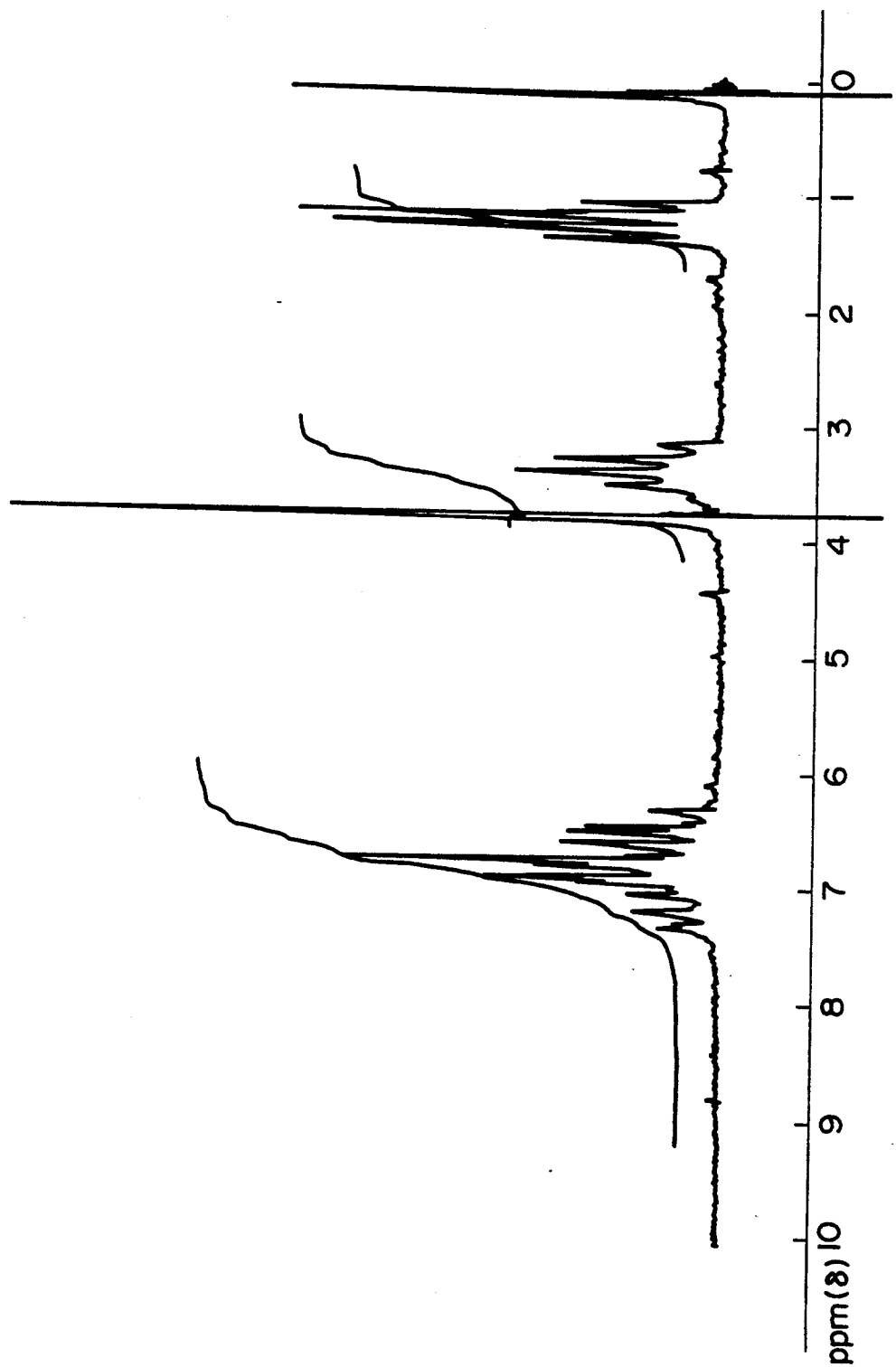
Figure 13:
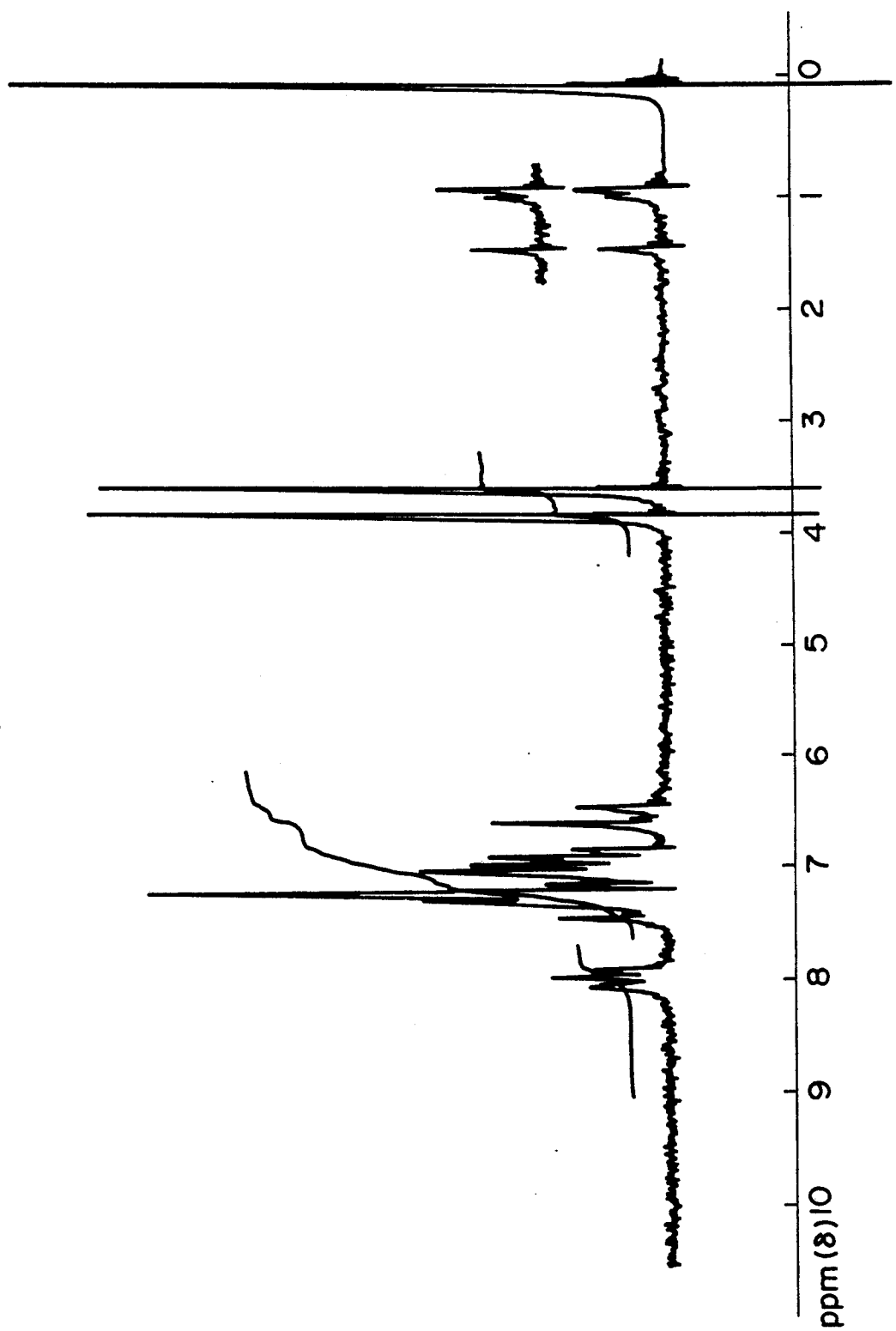
Figure 14:
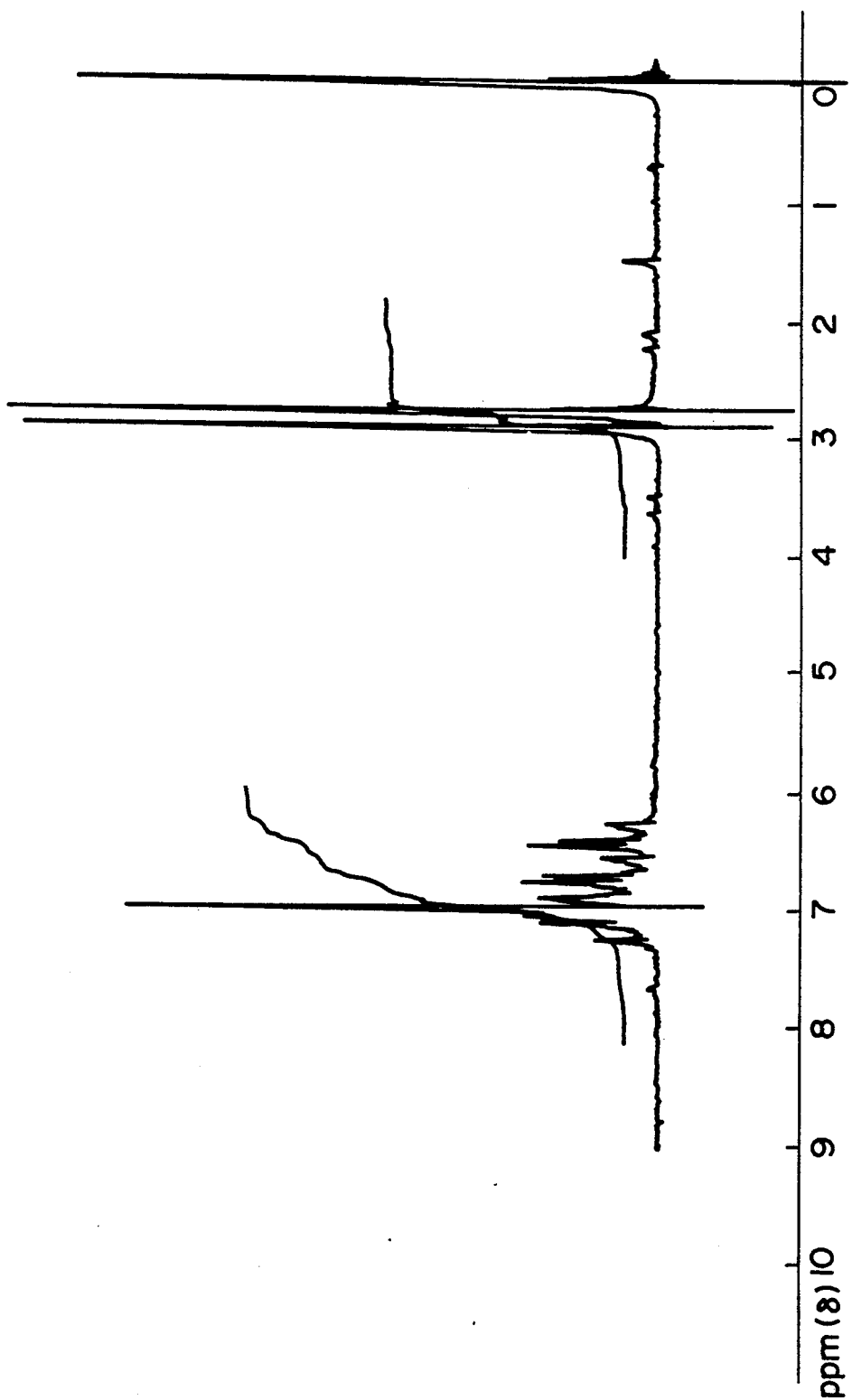
Figure 15:
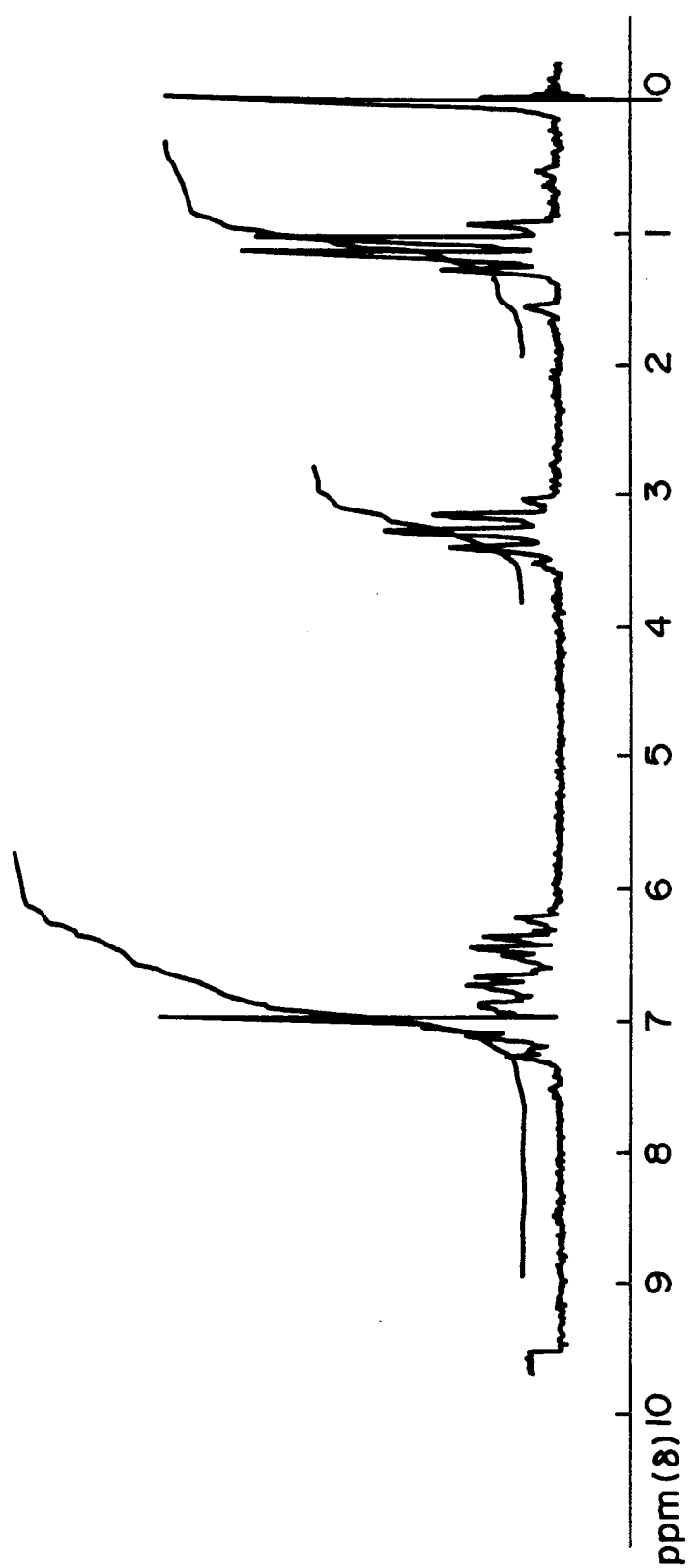

NMR spectrum of Compound (e) is shown in FIG. 10, and IR spectrum of Compound (e) is shown in FIG. 11.

SYNTHESIS EXAMPLE 6

[Synthesis of
1,1-bis(p-diethylaminophenyl)-2-[N,N-bis(p-methoxyphenyl) amino]ethylene: Compound 11]

Compound (b) in an amount of 19.6 g and 16.1 g of bis(p-anisyl)amine were dissolved in 350 ml of dry toluene. Then, 30 g of molecular sieves 4A and 0.2 g of p-toluenesulfonic acid were added thereto, followed by reflux for 2.5 hours. After cooling to room temperature, the reaction mixture was filtered. After removing the solvent by distillation, the resulting crystals were recrystallized from isopropyl ether (IPE) to give Compound having a melting point of 120°-122° C. in an amount of 15.8 g in 46% yield.

Maximum absorption wavelength: 308 nm ($\epsilon_{max}$ 3.50×10$^4$) (methanol)

| | Elementary analysis: | | |
|---|---|---|---|
| | C (%) | H (%) | N (%) |
| Calcd. | 78.18 | 6.77 | 8.55 |
| Found | 78.85 | 6.82 | 8.50 |

SYNTHESIS EXAMPLE b 7

[Synthesis of
1,1-bis(p-methoxyphenyl)-2-(9-carbazolyl)-aminoethylene: Compound 12]

A crude product of Compound 12 was synthesized from Compound (e) and carbazole in the same manner as described in Synthesis Example 6. After purifying with a silica gel column, recrystallization was conducted from IPE to give Compound 12 having a melting point of 201.5°-202.5° C. in 52% yield.

Maximum absorption wavelength: 252 nm ($\epsilon_{max}$ 4.50×10⁴) (methanol)

| | Elementary analysis: | | |
|---|---|---|---|
| | C (%) | H (%) | N (%) |
| Calcd. | 82.94 | 5.72 | 3.45 |
| Found | 82.96 | 5.76 | 3.41 |

SYNTHESIS EXAMPLE 8

[Synthesis of 1,1-bis(p-dimethylaminophenyl)-2-(N,N-diphenylamino)ethylene: Compound 13]

A crude product of compound 13 was synthesized from Compound (d) and diphenylamine in the same manner as described in Synthesis Example 6. After purifying with a silica gel column, recrystallization was conducted from IPE to give Compound 13 having a melting point of 141.5°-143° C. in 54% yield.

Maximum absorption wavelength: 301 nm ($\epsilon_{max}$ 3.51×10⁴) (methanol)

| | Elementary analysis: | | |
|---|---|---|---|
| | C (%) | H (%) | N (%) |
| Calcd. | 83.10 | 7.21 | 9.69 |
| Found | 83.29 | 7.26 | 9.70 |

SYNTHESIS EXAMPLE 9

[Synthesis of 1,1-bis(p-diethylaminophenyl)-2-(N,N-diphenylamino)ethylene: Compound 14]

A crude product of Compound 14 was synthesized from Compound (b) and diphenylamine in the same manner as described in Synthesis Example 6. After purifying with a silica gel column, recrystallization was conducted from IPE to give Compound 14 having a melting pint of 123°-124° C. in 39% yield.

Maximum absorption wavelength: 307 nm ($\epsilon_{max}$ 3.94×10⁴) (methanol)

| | Elementary analysis: | | |
|---|---|---|---|
| | C (%) | H (%) | N (%) |
| Calcd. | 83.39 | 8.03 | 8.58 |
| Found | 83.49 | 8.10 | 8.51 |

Compounds 11 to 14 obtained in Synthesis Examples 6 to 9 have the following belonging in NMR spectra:

| Belonging | Compound 11 | Compound 12 | Compound 13 | Compound 14 |
|---|---|---|---|---|
| —OCH₃ | | 3.6 s 3H | | |
| —OCH₃ | | 3.8 s 3H | | |
| —OCH₃ | 3.7 s 6H | | | |
| —NCH₃ | | | 2.8 s 6H | |
| —NCH₃ | | | 2.9 s 6H | |
| —NCH₂CH₃ | 1.05 t 6H | | | 1.05 t 6H |
| —NCH₂CH₃ | 1.10 t 6H | | | 1.15 t 6H |
| —NCH₂CH₃ | 3.05-3.50 | | | 3.2 q 4H |
| —NCH₂CH₃ | m 8H | | | 3.3 q 4H |
| arom. H | | 6.3-8.1 m 17H | 6.2-7.3 m 19H | 6.2-7.3 m 19H |
| | | Containing =CH— | Containing =CH— | Containing =CH— | Containing =CH— |

NMR spectra of Compounds 11 to 14 are shown in FIGS. 12 to 15, respectively.

As mentioned above, electrophotographic plates obtained by using the enamine derivatives of the formula (I) are excellent int eh sensitivity, photoresponse and durability.

What is claimed is:

1. An enamine derivative represented by the formula:

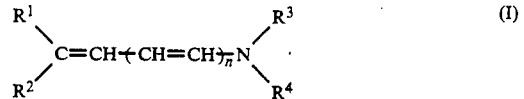

wherein R¹ is a group of the formula:

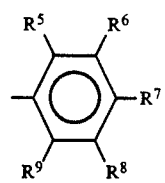

in which R⁵, R⁶, R⁷, R⁸ and R⁹ are independently hydrogen, a halogen atom, a straight- or branched-chain alkyl group having 1 to 9 carbon atoms, an aralkyl group, a straight- or branched-chain alkoxy group having 1 to 4 carbon atoms, an aryloxy group, an amino group substituted with one or two straight- or branched-chain alkyl groups having 1 to 9 carbon atoms, an amino group substituted with one or two aryl groups a hydroxy group, a nitro group or a cyano group; R², R³ and R⁴ are independently a straight- or branched-chain alkyl group having 1 to 9 carbon atoms, an aralkyl group, or an aryl group; and n is an integer of 1 or 2.

2. An anamine derivative according to claim 1, wherein said derivative is represented by the formula:

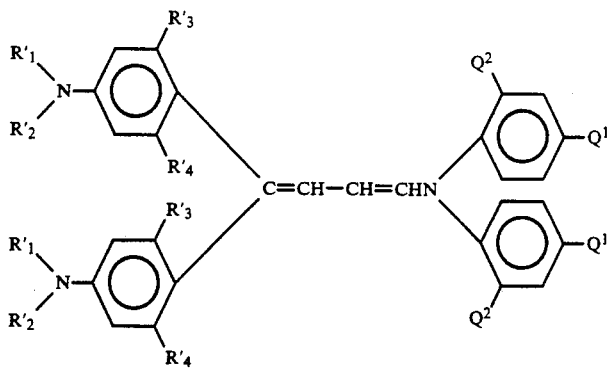

wherein R'₁ and R'₂ are independently a straight- or branched-chain alkyl group having 1 to 43 carbon atoms; R'₃ and R'₄ are independently hydrogen, a straight- or branched-chain alkyl group having 1 to 4 carbon atoms, an alkoxy group having 1 to 4 carbon atoms, or a halogen atom; $Q^1$ and $Q^2$ are independently hydrogen, a straight- or branched-chain alkyl group having 1 to 4 carbon atoms or a straight- or branched-chain alkoxy group having 1 to 4 carbon atoms.

3. An enamine derivative according to claim 1, wherein said derivative is represented by the formula:

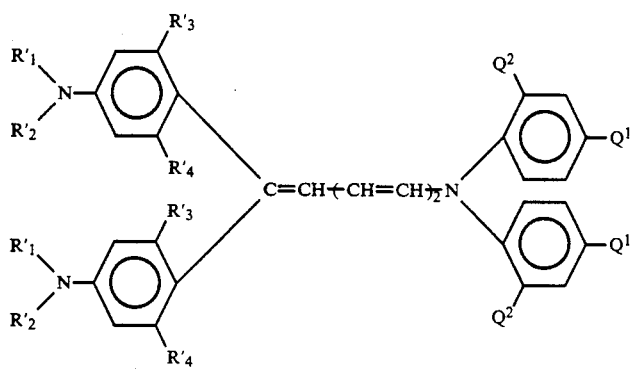

wherein R'₁ and R'₂₃ are independently a straight- or branched-chain alkyl group having 1 to 4 carbon atoms; R'₃ and R'₄ are independently hydrogen, a straight- or branched-chain alkyl group having 1 to 4 carbon atoms, an alkoxy group having 1 to 4 carbon atoms, or a halogen atom; $Q^1$ and $Q^2$ are independently hydrogen, a straight- or branched-chain alkyl group having 1 to 4 carbon atoms or a straight- or branched-chain alkoxy group having 1 to 4 carbon atoms.

4. An enamine derivative according to claim 2, which is a compound of the formula:

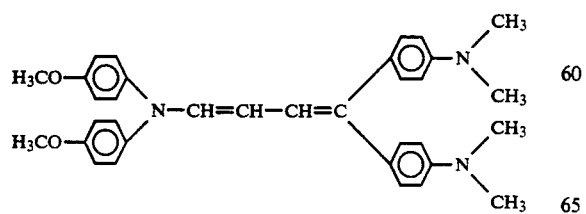

5. An anamine derivative according to claim 2, which is a compound of the formula:

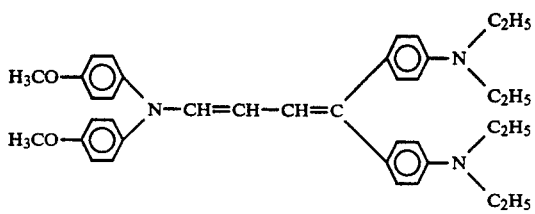

6. An enamine derivative according to claim 2, which is a compound of the formula:

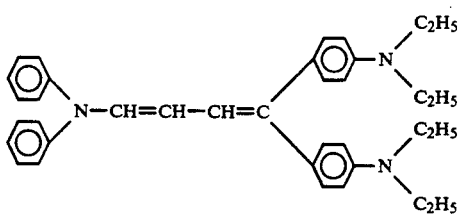

7. An enamine derivative according to claim 2, which is a compound of the formula:

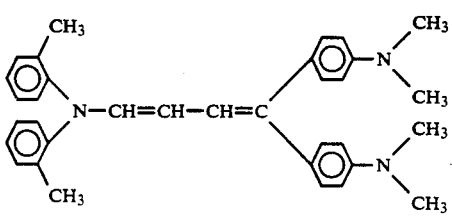

8. An enamine derivative according to claim 2, which is a compound of the formula:

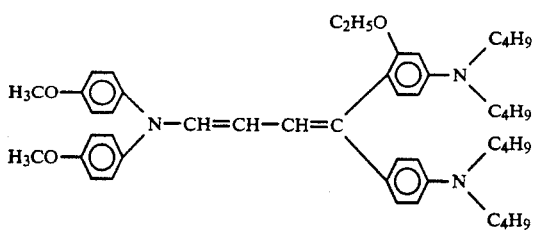

9. An enamine derivative according to claim 3, which is a compound of the formula:

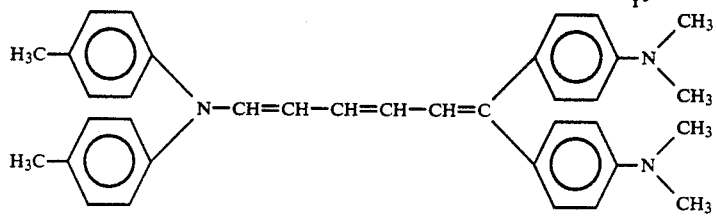

10. An enamine derivative according to claim 3, which is a compound of the formula:

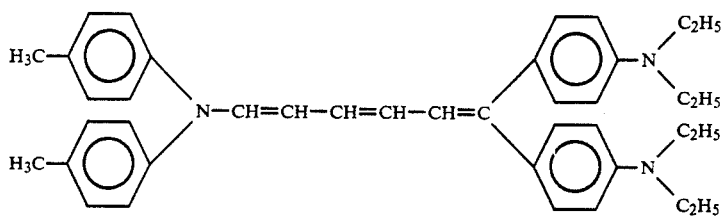

11. An enamine derivative according to claim 3, which is a compound of the formula:

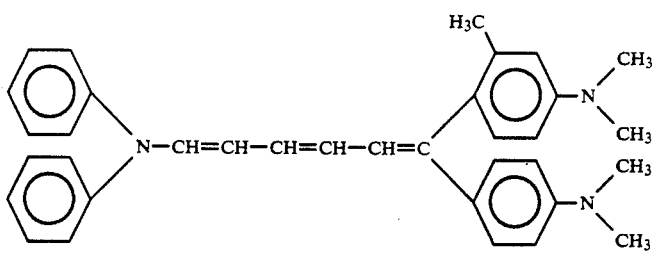

12. An enamine derivative according to claim 1, wherein $R^1$ is a group of the formula:

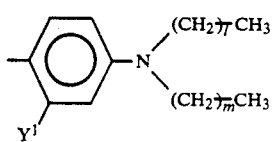

in which l is 0, 1, 2 or 3; m is 0, 1, 2 or 3 and $Y^1$ is hydrogen, methoxy or ethoxy; or

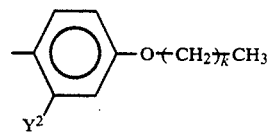

in which k is 0, 1, 2 or 3 and $Y^2$ is hydrogen, methoxy or ethoxy; or

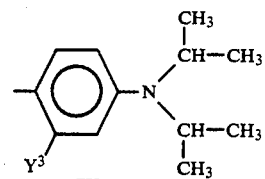

in which $Y^3$ is hydrogen, methoxy or ethoxy; or

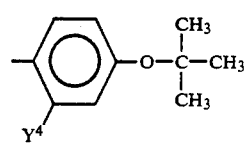

in which $Y^4$ is hydrogen, methoxy or ethoxy,

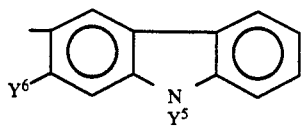

wherein R² is hydrogen, methyl, ethyl or a group of the formula:

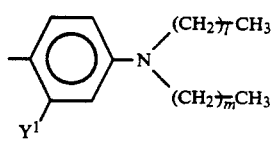

in which l, m and Y¹ are as defined above; or

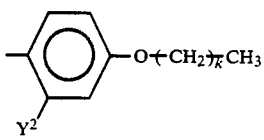

in which k and Y² are as defined above,

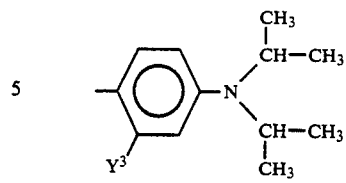

in which Y³ is as defined above; or

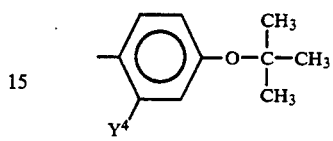

in which Y⁴ is as defined above,
wherein R³ and R⁴ independently represent a group of the formula:

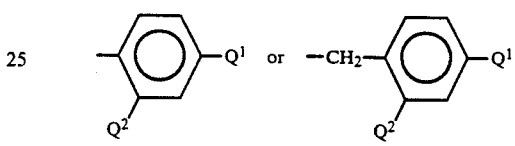

in which Q¹ and Q² are independently hydrogen, a straight- or branched-chain alkyl group having 1 to 4 carbon atoms, or a straight- or branched-chain alkoxy group having 1 to 4 carbon atoms.

* * * * *